(12) United States Patent
Weitz et al.

(10) Patent No.: US 9,695,390 B2
(45) Date of Patent: Jul. 4, 2017

(54) ACOUSTIC WAVES IN MICROFLUIDICS

(75) Inventors: David A. Weitz, Bolton, MA (US); Thomas Franke, Augsburg (DE); Achim Wixforth, Munich (DE); Lothar Schmid, Augsburg (DE); Jeremy Agresti, Richmond, CA (US); Adam R. Abate, San Francisco, CA (US)

(73) Assignees: President and Fellows of Harvard College, Cambridge, MA (US); Universität Augsburg, Augsburg (DE)

( * ) Notice: Subject to any disclaimer, the term of this patent is extended or adjusted under 35 U.S.C. 154(b) by 597 days.

(21) Appl. No.: 13/818,146

(22) PCT Filed: Aug. 23, 2011

(86) PCT No.: PCT/US2011/048804
§ 371 (c)(1),
(2), (4) Date: May 8, 2013

(87) PCT Pub. No.: WO2012/027366
PCT Pub. Date: Mar. 1, 2012

(65) Prior Publication Data
US 2013/0213488 A1    Aug. 22, 2013

Related U.S. Application Data

(60) Provisional application No. 61/376,137, filed on Aug. 23, 2010.

(51) Int. Cl.
*B01L 3/00* (2006.01)
*C12M 3/06* (2006.01)
(Continued)

(52) U.S. Cl.
CPC ....... *C12M 23/16* (2013.01); *B01L 3/502761* (2013.01); *B01L 3/502776* (2013.01);
(Continued)

(58) Field of Classification Search
CPC . C12M 23/16; C12M 47/04; B01L 3/502761; B01L 3/502776
See application file for complete search history.

(56) References Cited

U.S. PATENT DOCUMENTS 5,512,131 A    4/1996  Kumar et al.
5,688,405 A    11/1997 Dickinson et al.
(Continued)

FOREIGN PATENT DOCUMENTS

CN    101099727 A    1/2008
EP    1398025 A1    3/2004
(Continued)

OTHER PUBLICATIONS

International Search Report and Written Opinion for Application No. PCT/US2011/048804 mailed Apr. 10, 2012.
(Continued)

*Primary Examiner* — Melanie Y Brown
(74) *Attorney, Agent, or Firm* — Wolf, Greenfield & Sacks, P.C.

(57) ABSTRACT

Various aspects of the present invention relate to the control and manipulation of fluidic species, for example, in microfluidic systems. In one set of embodiments, droplets may be sorted using surface acoustic waves. The droplets may contain cells or other species. In some cases, the surface acoustic waves may be created using a surface acoustic wave generator such as an interdigitated transducer, and/or a material such as a piezoelectric substrate. The piezoelectric substrate may be isolated from the microfluidic substrate except at or proximate the location where the droplets are sorted, e.g., into first or second microfluidic channels. At such locations, the microfluidic substrate may be coupled to the piezoelectric substrate (or other material) by one or more coupling regions. In some cases, relatively high sorting rates may be achieved, e.g., at rates of at least about 1,000 Hz, at
(Continued)

least about 10,000 Hz, or at least about 100,000 Hz, and in some embodiments, with high cell viability after sorting.

8 Claims, 12 Drawing Sheets

(51) Int. Cl.
    *C12M 1/00*      (2006.01)
    *F17D 3/01*      (2006.01)
    *G01N 15/10*      (2006.01)

(52) U.S. Cl.
CPC ............... *C12M 47/04* (2013.01); *F17D 3/01* (2013.01); *B01L 2200/0636* (2013.01); *B01L 2200/0652* (2013.01); *B01L 2300/0816* (2013.01); *B01L 2400/0421* (2013.01); *B01L 2400/0436* (2013.01); *B01L 2400/0487* (2013.01); *B01L 2400/0496* (2013.01); *G01N 2015/1006* (2013.01); *G01N 2015/1081* (2013.01); *Y10T 137/0391* (2015.04)

(56) References Cited

U.S. PATENT DOCUMENTS

| | | | |
|---|---|---|---|
| 6,355,198 B1 | 3/2002 | Kim et al. | |
| 6,777,245 B2 | 8/2004 | Wixforth | |
| 7,708,949 B2 | 5/2010 | Stone et al. | |
| 7,942,568 B1* | 5/2011 | Branch | B01F 11/0266 366/127 |
| 8,573,060 B2* | 11/2013 | Huang et al. | 73/570.5 |
| 8,765,485 B2 | 7/2014 | Link et al. | |
| 2001/0055529 A1* | 12/2001 | Wixforth | 417/53 |
| 2004/0069717 A1* | 4/2004 | Laurell | A61M 1/3472 210/748.05 |
| 2005/0172476 A1 | 8/2005 | Stone et al. | |
| 2006/0163385 A1 | 7/2006 | Link et al. | |
| 2007/0003442 A1 | 1/2007 | Link et al. | |
| 2007/0054119 A1 | 3/2007 | Garstecki et al. | |
| 2007/0125941 A1* | 6/2007 | Lee | B01L 3/502761 250/251 |
| 2007/0206055 A1 | 9/2007 | Zapka et al. | |
| 2009/0226994 A1* | 9/2009 | Lemor | B01L 3/502715 435/173.1 |
| 2010/0139377 A1 | 6/2010 | Huang et al. | |
| 2010/0200092 A1* | 8/2010 | Beltram | B01L 3/502707 137/828 |
| 2010/0248064 A1 | 9/2010 | La O' et al. | |
| 2011/0032528 A1* | 2/2011 | Charette | G01N 21/553 356/445 |
| 2011/0127164 A1 | 6/2011 | Sinha et al. | |
| 2011/0275143 A1 | 11/2011 | Prakash et al. | |
| 2011/0277848 A1 | 11/2011 | Burns et al. | |
| 2012/0146457 A1* | 6/2012 | Goto | H03H 9/0222 310/313 B |
| 2012/0149126 A1 | 6/2012 | Wilson et al. | |
| 2012/0160746 A1* | 6/2012 | Thorslund et al. | 209/552 |
| 2013/0213488 A1 | 8/2013 | Weitz et al. | |
| 2014/0008307 A1 | 1/2014 | Guldiken et al. | |
| 2015/0192546 A1 | 7/2015 | Weitz et al. | |
| 2015/0298157 A1 | 10/2015 | Weitz et al. | |

FOREIGN PATENT DOCUMENTS

| | | |
|---|---|---|
| EP | 1 905 427 A1 | 4/2008 |
| EP | 2014280 A1 | 1/2009 |
| JP | 7304997 A | 11/1995 |
| JP | 2004161739 A | 6/2004 |
| JP | 4472002 B2 | 6/2010 |
| WO | WO 96/29629 A2 | 9/1996 |
| WO | WO 98/06667 A1 | 2/1998 |
| WO | WO 01/05731 A1 | 1/2001 |
| WO | WO 01/89787 A2 | 11/2001 |
| WO | WO 2004/002627 A2 | 1/2004 |
| WO | WO 2004/048356 A1 | 6/2004 |
| WO | WO 2004/091763 A2 | 10/2004 |
| WO | WO 2005/021151 A1 | 3/2005 |
| WO | WO 2005/037267 A1 | 4/2005 |
| WO | WO 2006/096571 A2 | 9/2006 |
| WO | WO 2007/128045 A1 | 11/2007 |
| WO | WO 2007/141002 A1 | 12/2007 |
| WO | WO 2008/000042 A1 | 1/2008 |
| WO | WO 2008/072155 A1 | 6/2008 |
| WO | WO 2009/077147 A2 | 6/2009 |
| WO | WO 2010/121328 A1 | 10/2010 |
| WO | WO 2012/027366 A2 | 3/2012 |
| WO | WO 2012/098140 A1 | 7/2012 |
| WO | WO 2012/135259 A1 | 10/2012 |
| WO | WO 2014/004630 A1 | 1/2014 |
| WO | WO 2014/066624 A1 | 5/2014 |

OTHER PUBLICATIONS

International Preliminary Report on Patentability for Application No. PCT/US2011/048804 mailed Mar. 7, 2013.
Franke et al., Surface acoustic wave (SAW) directed droplet flow in microfluidics for PDMS devices. Lab Chip. Sep. 21, 2009;9(18):2625-7.
Franke et al., Surface acoustic wave actuated cell sorting (SAWACS). Lab Chip. Mar. 21, 2010;10(6):789-94.
Ravula et al., A microfluidic system combining acoustic and dielectrophoretic particle preconcentration and focusing. Sensors and Actuators B: Chemical. Mar. 28, 2008;130(2):645-52.
Schmid et al., Novel surface acoustic wave (SAW)-driven closed PDMS flow chamber. Microfluidics and Nanofluidics. Jan. 2012;12(1-4):229-35.
Shi et al., Focusing microparticles in a microfluidic channel with standing surface acoustic waves (SSAW). Lab Chip. Feb. 2008;8(2):221-3.
Tsutsui et al., Cell Separation by Non-Inertial Force Fields in Microfluidic Systems. Mech Res Commun. Jan. 1, 2009;36(1):92-103.
Wood et al., Formation and manipulation of two-dimensional arrays of micron-scale particles in microfluidic systems by surface acoustic waves. Applied Physics Letters. Aug. 2009;94(5):054101.
International Search Report and Written Opinion for Application No. PCT/US2013/047829 mailed Sep. 9, 2013.
International Preliminary Report on Patentability for Application No. PCT/US2013/047829 mailed Jan. 8, 2015.
International Search Report and Written Opinion for Application No. PCT/US2013/066591 mailed Mar. 11, 2014.
Abate et al., High-throughput injection with microfluidics using picoinjectors. Proc Natl Acad Sci U S A. Nov. 9, 2010;107(45):19163-6. doi: 10.1073/pnas.1006888107. Epub Oct. 20, 2010.
Schmid et al., Acoustic modulation of droplet size in a T-junction. Applied Physics Letters. Mar. 31, 2014;104(13):133501-4. DOI: 10.1063/1.4869536.
Schmid et al., SAW-controlled drop size for flow focusing. Lab Chip. May 7, 2013;13(9):1691-4. doi: 10.1039/c3lc41233d.
International Search Report and Written Opinion for Application No. PCT/US2015/037662 mailed Sep. 18, 2015.
Collins et al., The particle valve: On-demand particle trapping, filtering, and release from a microfabricated polydimethylsiloxane membrane using surface acoustic waves. Applied Physics Letters. Jul. 2014;105:33509.

* cited by examiner

50 μm

50 μm

| FREQUENCY | $\varphi_{COLLECT}$ | $\varphi_{WASTE}$ | $\varphi_{ON-OFF}$ | $\varphi_{OFF-ON}$ | COLLECT | WASTE | # CELLS |
|---|---|---|---|---|---|---|---|
| MV3 CELLS (25 dBm) | | | | | | | |
| 200 Hz | 0.45 | 0.40 | 0.10 | 0.05 % | 100 % | 100 % | 175 |
| 400 Hz | 0.60 | 0.20 | 0.08 | 0.12 % | 100 % | 100 % | 90 |
| 400 Hz | 0.30 | 0.44 | 0.08 | 0.18 % | 100 % | 100 % | 91 |
| 1000 Hz | (0.50) | (0.50) | -- | -- | 78 % | 81 % | 149 |
| 2000 Hz | (0.60) | (0.40) | -- | -- | 76 % | 69 % | 315 |
| MOUSE FIBROBLAST CELLS (33 dBm) | | | | | | | |
| 2000 Hz | 0.28 | 0.56 | 0.04 | 0.12 | 100 % | 100 % | 179 |
| 4000 Hz | (0.60) | (0.40) | -- | -- | 79 % | 64 % | 87 |
| HaCat CELLS (28 dBm) | | | | | | | |
| 1000 Hz | 0.08 | 0.17 | 0.33 | 0.42 | 100 % | 100 % | 136 |
| 2000 Hz | (0.67) | (0.33) | -- | -- | 76 % | 57 % | 208 |

Fig. 4B

From Fig. 5A

From Fig. 5B

ACOUSTIC WAVES IN MICROFLUIDICS

GOVERNMENT FUNDING

This invention was made with government support under Grant Nos. DMR-0602684 and DMR-0820484 awarded by the National Science Foundation. The government has certain rights in the invention.

RELATED APPLICATIONS

This application is a national stage filing of International Patent Application Serial No. PCT/US2011/048804, filed Aug. 23, 2011, entitled "Acoustic Waves In Microfluidics," by Weitz, et al., claims the benefit of U.S. Provisional Patent Application Ser. No. 61/376,137, filed Aug. 23, 2010, entitled "Acoustic Waves in Microfluidics," by Weitz, et al., each incorporated herein by reference.

FIELD OF INVENTION

The present invention generally relates to acoustic waves in microfluidics, including surface acoustic waves.

BACKGROUND

Cell sorting is of tremendous importance not only for basic cell biology but also for clinical medicine, cancer research, reproductive medicine or transplantation immunology. Modern cell sorting schemes operate in several different ways. For example, cells may be sorted in continuous flow or encapsulated in small liquid droplets prior to sorting. In the latter case, the problem of sorting applies to the droplets and not to the cells. Droplets can be sorted, for instance, in air or in another immiscible continuous liquid. Traditional fluorescence activated cell sorters ("FACS") encapsulate cells in droplets, which are then labeled with an electric charge and subsequently separated in an electric field. These sorters reach very high sorting rates, but have several disadvantages including high costs and large dead volume, which make it nearly impossible to separate cells from small sample volumes. Moreover, elaborate cleaning and maintenance procedures are necessary to prevent cross-contamination of different samples, making handling more difficult.

These drawbacks can be avoided using low cost disposable microfluidic devices which operate at small sample volumes. In such devices, highly monodisperse aqueous droplets enclosing the cells can be produced at very high rates in an immiscible continuous oil phase instead of air. Such emulsions can even be prepared having higher hierarchies, e.g., in so-called "multiple emulsions," containing droplets in droplets. In single emulsions, the objects to be sorted (e.g., cells) can be distinguished from the bulk solution, for example, because of their inherent contrast in material properties of the aqueous and oil phases. This contrast can be exploited for sorting in some cases. Most commonly used is the polarizability contrast in dielectrophoretic sorters. Other sorters can be found in U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, incorporated herein by reference.

However, many droplet-enhanced sorters come with an additional processing step of loading cells into the droplets. In some cases, enclosing the cells in droplets may not be desirable; for example, if the cells are to be cultured after sorting, they must be first removed from the emulsion.

In contrast to droplet sorting, direct cell-sorting schemes operating in the continuous phase have to deal with low contrast of material properties of cells and the bulk solution containing the cells, as both typically appear as aqueous liquids. To overcome this limitation, responsive beads are often biochemically attached to the cells to enhance the separation efficiency. For example, in magnetic activated cell sorting (MACS), a magnetic bead is selectively adhered to a target cell prior to sorting the cell using a magnetic field. Also, attachment of polarizable beads has been used to subsequently separate the target and waste cells in an electric field gradient. Optical force switching has been used for sorting as well but suffers from relatively slow sorting rates.

There are also a few techniques that utilize hydrodynamic flow to sort cells such as syringe enhanced pumping or electrokinetic mobilization. Typically, they all suffer from slow response times and consequently low sorting rates or low cell viability under high electric fields.

Accordingly, improvements in cell sorting devices and methods are needed.

SUMMARY OF THE INVENTION

The present invention generally relates to acoustic waves in microfluidics. The subject matter of the present invention involves, in some cases, interrelated products, alternative solutions to a particular problem, and/or a plurality of different uses of one or more systems and/or articles.

In one aspect, the present invention is generally directed to a method comprising sorting cells in a microfluidic device using surface acoustic waves. In another aspect, the present invention is generally directed to a method comprising providing a plurality of droplets, at least some of which contain cells, directing the plurality of droplets through an inlet microfluidic channel to a junction between a first channel and a second channel, thereby sorting the droplets, and applying a surface acoustic wave at some of the droplets to cause those droplets to enter the first channel. In some cases, in the absence of the surface acoustic wave, the droplets enter the second channel.

The method, in another set of embodiments, includes acts of directing a plurality of droplets through an inlet microfluidic channel to a single junction between the inlet microfluidic channel, a first channel, a second channel, and a third channel, and applying a first surface acoustic wave to some of the droplets to cause the droplets to enter the first channel and applying a second surface acoustic wave to some of the droplets to cause the droplets to enter the second channel, where in the absence of the first or second surface acoustic waves, the droplets enter the third channel. In yet another set of embodiments, the method includes acts of directing a plurality of droplets through an inlet microfluidic channel to a single junction between the inlet microfluidic channel, and more than two outlet channels, and applying a surface acoustic wave to some of the droplets to cause the droplets to enter one channel of the more than two outlet channels.

In another set of embodiments, the method includes acts of providing a plurality of droplets, at least some of which contain cells, directing the plurality of droplets through an inlet microfluidic channel to a junction between the inlet microfluidic channel, a first channel and a second channel, and applying a surface acoustic wave to some of the droplets to cause the droplets to enter the first channel, where in the absence of the surface acoustic wave, the droplets enter the second channel.

According to another aspect, the present invention is generally directed to an article comprising a microfluidic substrate having defined therein a microfluidic system containing an inlet microfluidic channel, a first channel, and a second channel meeting at a junction; and an interdigitated transducer positioned to direct surface acoustic waves at the junction.

In another set of embodiments, the article includes a microfluidic substrate having defined therein a microfluidic system containing an inlet microfluidic channel and more than two outlet channels meeting at a single junction, a tapered interdigitated transducer positioned on a material, and at least two coupling regions, each of which is positioned to refract surface acoustic waves generated by the tapered interdigitated transducer towards at least a portion of the single junction. In some cases, each coupling region physically connects the material and the microfluidic substrate.

The article, in yet another set of embodiments, includes a microfluidic substrate having defined therein a microfluidic system containing an inlet microfluidic channel, a first channel, and a second channel meeting at a junction, a surface acoustic wave generator positioned on a piezoelectric substrate, and a coupling region positioned to refract surface acoustic waves generated by the surface acoustic wave generator towards at least a portion of the junction. The coupling region may physically connect the microfluidic substrate and the material.

In another aspect, the present invention encompasses methods of making one or more of the embodiments described herein. In still another aspect, the present invention encompasses methods of using one or more of the embodiments described herein.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 4A-4B illustrate phase data in yet another embodiment of the invention;

DETAILED DESCRIPTION

Figure 1A:
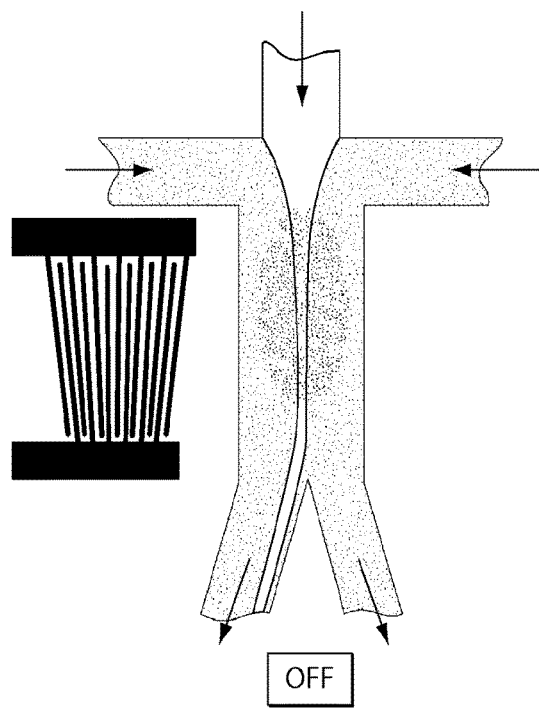
FIGS. 1A-1D illustrate techniques to sort cells using surface acoustic waves, in accordance with one embodiment of the invention.

Various aspects of the present invention relate to the control and manipulation of fluidic species, for example, in microfluidic systems. In one set of embodiments, droplets may be sorted using surface acoustic waves. The droplets may contain cells or other species. In some cases, the surface acoustic waves may be created using a surface acoustic wave generator such as an interdigitated transducer, and/or a material such as a piezoelectric substrate. The piezoelectric substrate may be isolated from the microfluidic substrate except at or proximate the location where the droplets are sorted, e.g., into first or second microfluidic channels. At such locations, the microfluidic substrate may be coupled to the piezoelectric substrate (or other material) by one or more coupling regions. In some cases, relatively high sorting rates may be achieved, e.g., at rates of at least about 1,000 Hz, at least about 10,000 Hz, or at least about 100,000 Hz, and in some embodiments, with high cell viability after sorting.

In one aspect, the invention provides systems and methods for sorting fluidic droplets in a liquid, and in some cases, at relatively high rates. For example, a characteristic of a droplet may be sensed and/or determined in some fashion (e.g., as further described herein), then the droplet may be directed towards a particular region of the device, such as a microfluidic channel, for example, for sorting purposes.

In some embodiments, a characteristic of a fluidic droplet may be sensed and/or determined in some fashion (e.g., fluorescence of the fluidic droplet may be determined), and, in response, an acoustic wave may be applied to the microfluidic channel to direct the fluidic droplet to a particular region (e.g. a channel). In some cases, high sorting speeds may be achievable using certain systems and methods of the invention. For instance, at least about 10 droplets per second may be determined and/or sorted in some cases, and in other cases, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1,000 droplets per second, at least about 1,500 droplets per second, at least about 2,000 droplets per second, at least about 3,000 droplets per second, at least about 5,000 droplets per second, at least about 7,500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second, at least about 1,500,000 droplets per second, at least about 2,000,000 or more droplets per second, or at least about 3,000,000 or more droplets per second may be determined and/or sorted in such a fashion.

Certain embodiments of the present invention are directed to sorting cells in a microfluidic device using surface acoustic waves. A surface acoustic wave ("SAW") is, generally speaking, an acoustic wave able to travel along the surface of a material exhibiting elasticity, with an amplitude that typically decays exponentially with depth into the material. The surface acoustic wave may have any suitable average frequency. For example, the average frequency of the surface acoustic wave may be between about 100 MHz and about 200 MHz, between about 130 MHz and about 160 MHz, between about 140 MHz and about 150 MHz, between about 100 MHz and about 120 MHz, between about 120 MHz and about 140 MHz, between about 140 MHz and about 160 MHz, between about 160 MHz and about 180 MHz, or between about 180 MHz and about 200 MHz or the like, and/or combinations thereof.

Any suitable technique may be used to create a surface acoustic wave. For example, the surface acoustic wave may be created by a generator attached to the surface of a material. In certain embodiments, the surface acoustic wave is created by using an interdigitated electrode or transducer able to convert electrical signals into acoustic waves able to travel along the surface of a material, and in some cases, the frequency of the surface acoustic waves may be controlled by controlling the spacing of the finger repeat distance of the interdigitated electrode or transducer. The surface acoustic waves can be formed on a piezoelectric substrate or other material that may be coupled to a microfluidic substrate at specific locations, e.g., at locations within the microfluidic substrate where sorting is to take place. Suitable voltages (e.g., sinusoidal or other periodically varying voltages) are applied to the piezoelectric substrate, which converts the electrical signals into mechanical vibrations, i.e., surface acoustic waves or sound. The sound is then coupled to the microfluidic substrate, e.g., from the surface of the material. In the microfluidic substrate, the vibrations pass into liquid within microfluidic channels in the microfluidic substrate (e.g., liquid containing droplets containing cells or other species to be sorted), which give rise to internal streaming within the fluid. Thus, by controlling the applied voltage, streaming within the microfluidic channel may be controlled, which may be used to direct or sort droplets within the microfluidic channel, e.g., to particular regions within the microfluidic substrate.

Figure 1B:
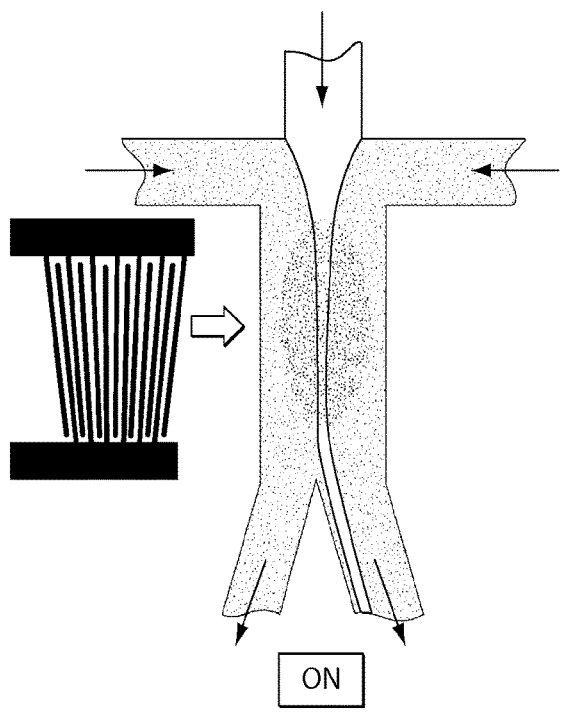
Figure 1C:
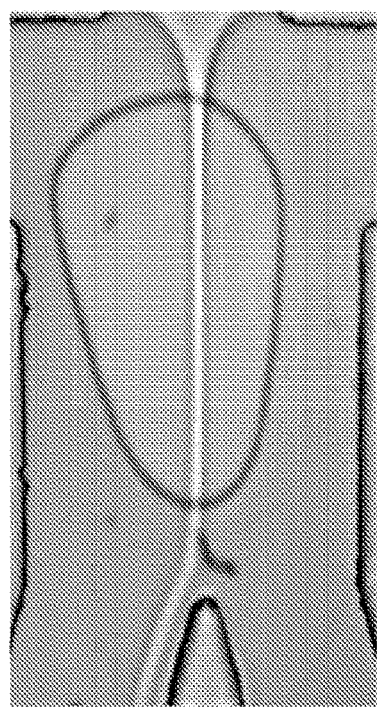
Figure 1D:
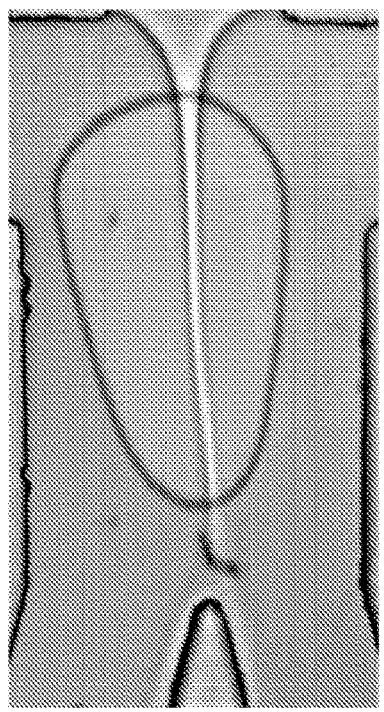

An interdigitated transducer typically comprises one, two, or more electrodes containing a plurality of "fingers" extending away from the electrode, wherein at least some of the fingers are interdigitated. The fingers may be of any length, and may independently have the same or different lengths. The fingers may be spaced on the transducer regularly or irregularly. In some cases, the fingers may be substantially parallel, although in other embodiments they need not be substantially parallel. For example, in one set of embodiments, the interdigitated transducer is a tapered interdigitated transducer. In some cases, the fingers in a tapered interdigitated transducer may be arranged such that the fingers are angled inwardly, e.g., as shown in FIGS. 1A and 1B.

Such control of the internal streaming of the fluid can be used to control the movement of the fluid and/or droplets contained therein, for example such that the fluid can be directed to a first location (e.g., a first microfluidic channel) or a second location (e.g., a second microfluidic channel). In this way, for example, a plurality of droplets flowing in an inlet microfluidic channel towards a junction with a first microfluidic channel and a second microfluidic channel may be controlled such that the droplets can be controllably delivered to either microfluidic channel, for instance, by applying or not applying a suitable voltage to the piezoelectric substrate. As a specific non-limiting example, fluid may flow through the microfluidic channels such that, in the absence of a suitable surface acoustic wave, droplets contained within the fluid flow into a first channel, while in the presence of a suitable surface acoustic wave, some or all of the droplets contained within the fluid, as affected by the surface acoustic wave, flow into a second channel. It should be noted that control of the streaming properties of the fluid primarily affects the fluid itself, rather than any droplets or other species contained in the fluid. Accordingly, in various embodiments, no contrast in compressibility, dielectric constant, and/or density is necessarily required to be able to sort droplets contained within a fluid.

The interdigitated electrode typically includes of two interlocking comb-shaped metallic electrodes that do not touch, but are interdigitated. A schematic example of such an electrode is illustrated in FIGS. 1A and 1B. The electrodes may be formed from any suitable electrode material, for example, metals such as gold, silver, copper, nickel, or the like. The operating frequency of the interdigitated electrode may be determined, in some embodiments, by the ratio of the sound velocity in the substrate to twice the finger spacing. For instance, in one set of embodiments, the finger repeat distance may be between about 10 micrometers and about 40 micrometers, between about 10 micrometers and about 30 micrometers, between about 20 micrometers and about 40 micrometers, between about 20 micrometers and about 30 micrometers, or between about 23 micrometers and about 28 micrometers.

The interdigitated electrode may be positioned on a piezoelectric substrate, or other material able to transmit surface acoustic waves, e.g., to a coupling region. The piezoelectric substrate may be formed out of any suitable piezoelectric material, for example, quartz, lithium niobate, lithium tantalate, lanthanum gallium silicate, etc. In one set of embodiments, the piezoelectric substrate is anisotropic, and in some embodiments, the piezoelectric substrate is a Y-cut $LiNbO_3$ material.

The piezoelectric substrate may be activated by any suitable electronic input signal or voltage to the piezoelectric substrate (or portion thereof). For example, the input signal may be one in which a periodically varying signal is used, e.g., to create corresponding acoustic waves. For instance, the signals may be sine waves, square waves, sawtooth waves, triangular waves, or the like. The frequency may be for example, between about 50 Hz and about 100 KHz, between about 100 Hz and about 2 kHz, between about 100 Hz and about 1,000 Hz, between about 1,000 Hz and about 10,000 Hz, between about 10,000 Hz and about 100,000 Hz, or the like, and/or combinations thereof. In some cases, the frequency may be at least about 50 Hz, at least about 100 Hz, at least about 300 Hz, at least about 1,000 Hz, at least about 3,000 Hz, at least about 10,000 Hz, at least about 30,000 Hz, at least about 100,000 Hz, at least about 300,000 Hz, at least about 1 MHz, at least about 3 MHz, at least about 10 MHz, at least about 30 MHz, at least about 100 MHz, at least about 300 MHz, or at least about 1 GHz or more in some embodiments. In certain instances, the frequency may be no more than about 1 GHz, no more than about 300 MHz, no more than about 100 MHz, no more than about 30 MHz, no more than about 10 MHz, no more than about 3 MHz, no more than about 1 MHz, no more than about 300,000 Hz, no more than about 100,000 Hz, no more than about 30,000 Hz, no more than about 10,000 Hz, no more than about 3,000

Hz, no more than about 1,000 Hz, no more than about 300 Hz, no more than about 100 Hz, or the like.

The interdigitated electrode may be positioned on the piezoelectric substrate (or other suitable material) such that acoustic waves produced by the interdigitated electrodes are directed at a region of acoustic coupling between the piezoelectric substrate and the microfluidic substrate. For example, the piezoelectric substrate and the microfluidic substrate may be coupled or physically bonded to each other, for example, using ozone plasma treatment, or other suitable techniques. In some cases, the rest of the piezoelectric substrate and the microfluidic substrate are at least acoustically isolated from each other, and in certain embodiments, the piezoelectric substrate and the microfluidic substrate are physically isolated from each other. Without wishing to be bound by any theory, it is believed that due to the isolation, acoustic waves created by the interdigitated electrode and the piezoelectric substrate do not affect the microfluidic substrate except at regions where sorting is generally desired, e.g., at one or more coupling regions. Such acoustic coupling may be used, in certain embodiments, to increase sorting speed, e.g., due to better control of the passage of surface acoustic waves.

In one set of embodiments, the coupling region of the piezoelectric substrate and the microfluidic substrate is located within or proximate the location where droplets or other species are to be sorted within the microfluidic substrate. Thus, for instance, the coupling region may be positioned within or at least near a junction between an inlet microfluidic channel, and two or more outlet microfluidic channels, such that acoustic waves transmitted into the microfluidic substrate through the coupling region are at least sufficient to affect liquid streaming within the microfluidic channels, and in some embodiments such that sorting of droplets or other species is able to occur. In one set of embodiments, there may be three, four, five, or more outlet microfluidic channels, and in some embodiments the sorting of droplets or other species into the two or more outlet microfluidic channels may be controlled by controlling the surface acoustic waves, e.g., by applying suitable voltages to the piezoelectric substrate, as discussed herein.

Figure 2A:
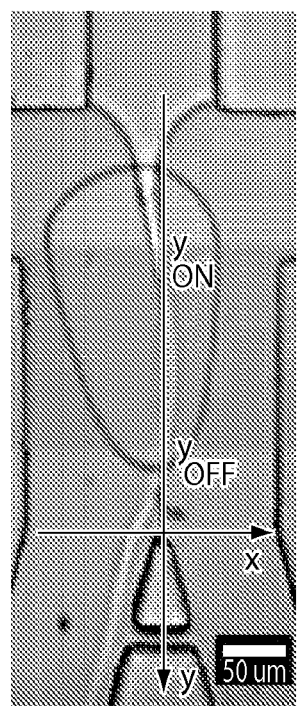
FIGS. 2A-2B illustrate sorting as a function of position, in another embodiment of the invention.

As a specific non-limiting example, FIG. 2A illustrates a coupling region between $y_{ON}$ and $y_{OFF}$, where fluid flows within this region may be controlled. The interdigitated electrode may be positioned in any suitable location within the piezoelectric substrate (or other suitable material) such that surface acoustic waves produced by the interdigitated electrode are at least partially directed towards the coupling region. For example, in FIGS. 1A and 1B, the interdigitated electrodes are positioned on one side of the coupling region, in a lateral position relative to the flow of fluid in the microfluidic channel passing proximate the coupling region.

The coupling region may have any suitable shape and/or size. In one set of embodiments, the coupling region may have a size such that it includes a first location where droplets of fluid are created, and a second location where the droplets are sorted into first and second regions or channels. In other embodiments, the coupling region may be larger or smaller than this. In one set of embodiments, the coupling region is sized to be contained within a microfluidic channel, for example, as is illustrated in FIGS. 1A and 1B as non-limiting examples. The coupling region may be round, oval, or have other shapes, depending on the embodiment. In some cases, two, three, or more coupling regions may be used.

In some cases, control of the droplets into one of the channels may be achieved by using a tapered interdigitated transducer. A tapered interdigitated transducer may allow relatively high control of the location at which a SAW is applied to a channel, in contrast to an interdigitated transducer where all of the fingers are parallel to each other and the spacing between electrodes is constant. Without wishing to be bound by any theory, it is believed that the location which a SAW can be applied by an interdigitated transducer is controlled, at least in part, by the spacing between the electrodes. By controlling the potential applied to the interdigitated transducer, and thereby controlling the resonance frequency of the applied SAW, the position and/or the strength of the SAW as applied by the interdigitated transducer may be correspondingly controlled. Thus, for example, applying a first voltage to an interdigitated transducer may cause a first resonance frequency of the resulting SAW to be applied (e.g., within a channel), while applying a second voltage may cause a second resonance frequency of the resulting SAW to be applied to a different location (e.g., within the channel). As another example, a plurality of coupling regions may be used, e.g., in combination with one or more tapered interdigitated transducers, to control the exact location and nature of deflection of a droplet, e.g., to direct the droplet to two, three, or more channels.

Figure 7A:
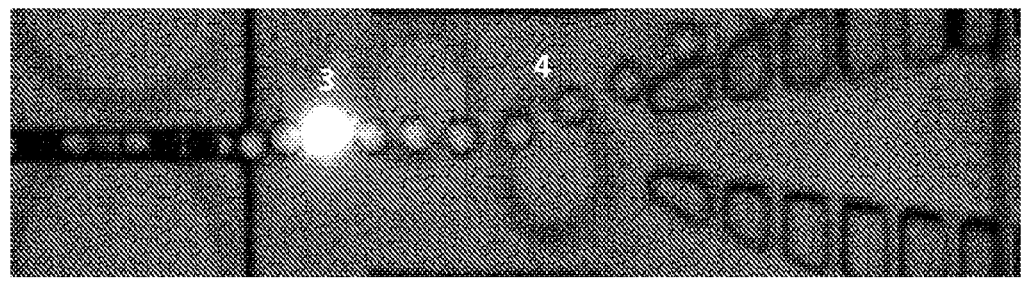
FIGS. 7A-7C illustrate the sorting of droplets into 3 different channels, in still another set of embodiments.
Figure 7B:
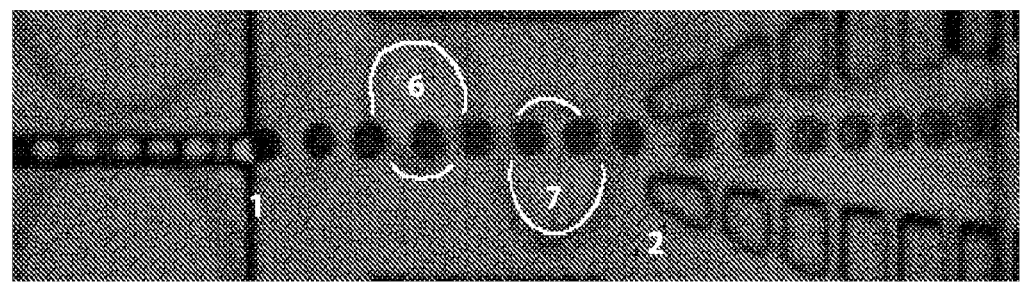
Figure 7C:
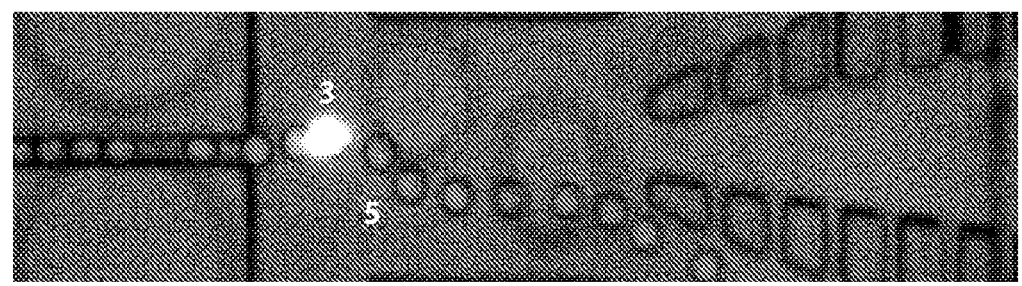

One non-limiting example of such a system is illustrated in FIGS. 7A-7C, where droplets entering from the left are sorted into three different channels on the right (an upper channel, a middle channel, and a lower channel). By controlling the voltage applied to a single tapered interdigitated transducer (not shown), the resonance frequency of the applied SAW may be controlled, and in some cases, used to couple different coupling regions. Thus, for example, a first voltage may be applied to cause coupling with region 6, thereby deflecting a droplet into the upper channel (as is shown in FIG. 7A), while a second voltage may be applied to cause coupling with region 7, thereby deflecting a droplet into the lower channel (as is shown in FIG. 7C). In FIG. 7B, no voltage is applied to the tapered interdigitated transducer, and thus the droplet moves straight into the middle channel. In other embodiments, however, other systems may be used to control the deflection of droplets to multiple channels, for example, by controlling the strength of the applied SAW, by controlling the voltage or frequency of electrical potential applied to a transducer, by the use of multiple transducers including interdigitated transducers, by the use of multiple coupling regions, etc.

The microfluidic substrate may be any suitable substrate which contains or defines one or more microfluidic channels. For instance, as is discussed below, the microfluidic substrate may be formed out of polydimethylsiloxane, polytetrafluoroethylene, or other suitable elastomeric polymers, at least according to various non-limiting examples. In certain embodiments, the substrate contains at least an inlet channel, a first (outlet) channel, and a second (outlet) channel meeting at a junction, e.g., having a "Y" or a "T" shape. By suitable application of surface acoustic waves, droplets contained within a fluid flowing through the inlet channel may be directed into the first channel or second channel. In other embodiments, however, other configurations of channels and junctions may be used, e.g., as described herein. Droplets contained within microfluidic channels are discussed in detail below.

Droplets may be created within the microfluidic channels using any suitable technique, and in various embodiments, many different droplet creation techniques may be used. The droplets may be substantially the same size, or may not necessarily be substantially the same size. For instance, fluid may be directed into the microfluidic substrate from an external source where the droplets are created, and/or the droplets may be created within the microfluidic substrate, for example, using droplet-creation techniques such as fluid focusing (e.g., hydrodynamic fluid focusing) or the like. See also, for example, U.S. patent application Ser. No. 11/246, 911, filed Oct. 7, 2005, entitled "Formation and Control of Fluidic Species," by Link, et al., published as U.S. Patent Application Publication No. 2006/0163385 on Jul. 27, 2006; U.S. patent application Ser. No. 11/024,228, filed Feb. 28, 2004, entitled "Method and Apparatus for Fluid Dispersion," by Stone, et al., now U.S. Pat. No. 7,708,949, issued May 4, 2010; or U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007, each incorporated herein by reference in their entireties.

In one aspect, the present invention relates to the production or expulsion of a fluidic stream from a channel where the fluidic stream has a cross-sectional dimension that is smaller than a cross-sectional dimension of the channel outlet. In some cases, the present invention allows the production or expulsion of a fluidic stream from a channel to occur in a manner that provides unique control over the fluidic stream and/or unique combinations of fluid or materials, as further described herein. As an example, a fluidic stream may be manipulated using one or more structural elements in or near its path of flow. As another example, a fluidic stream being produced or expelled from the channel may be contacted with another fluid in some fashion to manipulate the fluidic stream. As yet another example, an externally applied field (e.g., an electric and/or a magnetic field) may be generated proximate the channel outlet and/or proximate a fluidic stream to manipulate the fluidic stream. Combinations of any of these and/or other systems and techniques, e.g., as further described herein, are also contemplated in the present invention. Furthermore, the size of the fluidic stream, including droplet sizes in discontinuous streams, can be very precisely controlled in some instances.

In some cases, the fluidic stream may have an average cross-sectional dimension smaller than about 90% of an average cross-sectional dimension of the channel, and in certain embodiments, smaller than about 80%, about 70%, about 60%, about 50%, about 40%, or about 30% of the average cross-sectional dimension of the channel. In other embodiments, the fluidic stream may have an average cross-sectional dimension smaller than about 20%, about 10%, about 5%, about 3%, about 1%, about 0.5%, about 0.3%, about 0.1%, about 0.05%, about 0.03%, or about 0.01% of the average cross-sectional dimension of the channel. The fluidic stream, in some embodiments, may be produced on the microscale, e.g., using a microfluidic channel. For instance, the fluidic stream may have an average cross-sectional dimension of less than about 1 mm, less than about 500 microns, less than about 300 microns, or less than about 100 microns. In some cases, the fluidic stream may have an average diameter of less than about 60 microns, less than about 50 microns, less than about 40 microns, less than about 30 microns, less than about 25 microns, less than about 10 microns, less than about 5 microns, less than about 3 microns, or less than about 1 micron.

In one set of embodiments, a structural element may be used to manipulate the fluidic stream in some fashion to produce a fluidic stream that has a cross-sectional dimension that is smaller than a cross-sectional dimension of a channel outlet that produces the fluid. In some cases, a fluidic stream may be produced where no cross-sectional dimension of the fluidic stream has a dimension that is larger than the smallest cross-sectional dimension of the channel outlet. A "structural element," as used herein, is a physical feature, in or proximate the channel, that is able to at least partially alter fluid flow from the channel. Examples of structural elements include dimensional restrictions, ridges, grooves, or the like. As used herein, a "dimensional restriction" is a structural element that is shaped to reduce a cross-sectional dimension of the fluidic stream. In some cases, the dimensional restriction is an annular orifice, but it can also take any of a variety of forms, for example, elongate, ovoid, square, triangular, or the like. The dimensional restriction is non-valved in preferred embodiments. That is, the dimensional restriction is an orifice that cannot be switched between an open state and a closed state, and is typically of fixed size. As an example, the fluid, after passing through the dimensional restriction, may become a discontinuous stream of fluid. Other examples of dimensional restrictions can be seen in International Patent Application No. PCT/US03/20542, filed Jun. 30, 2003, entitled "Method and Apparatus for Fluid Dispersion," by Stone, et al., incorporated herein by reference.

In some cases, the fluidic stream and/or the surrounding fluid has a mean cross-sectional dimension no smaller than 90% of the average cross-sectional dimension of the dimensional restriction, and in other embodiments, no smaller than 80%, 70%, 60%, 50%, 40%, or 30% of the average cross-sectional dimension of the dimensional restriction. This can be advantageous in certain cases in that a system of the invention can be operated over a range of fluid flowrates, and still produce a fluidic stream having the same, or approximately the same, size or cross-sectional dimension.

In another set of embodiments, one or more additional fluidic streams may be used to manipulate the fluidic stream in some fashion to produce a fluidic stream that has a cross-sectional dimension that is smaller than a cross-sectional dimension of a channel outlet that produces the fluid. The second fluid may be directed at the fluid and/or at the channel in such a way as to cause the fluidic stream produced by the channel to have a cross-sectional dimension smaller than a cross-sectional dimension of a channel outlet, and in some cases, such that no cross-sectional dimension of the fluidic stream has a dimension that is larger than the smallest cross-sectional dimension of the channel. In one embodiment, an additional fluid or fluids are directed in such a way as to surround or "sheath" the fluid being produced by the channel, reducing a cross-sectional dimension of the fluidic stream. The invention, in some cases, thus involves control over the average cross-sectional dimensions of the fluidic stream by control of the flowrate of a sheathing fluid, and/or control of the ratios of the flowrate of the fluidic stream relative to the sheathing fluid.

In some embodiments, an externally applied field (e.g., an electric and/or a magnetic field) may be generated proximate the channel outlet and/or proximate a fluidic stream to manipulate the fluidic stream, for example, to produce a fluidic stream that has a cross-sectional dimension that is smaller than a cross-sectional dimension of a channel outlet that produces the fluid. In one embodiment, the externally applied field includes a magnetic field. Techniques for producing suitable magnetic fields are known to those of ordinary skill in the art, for example, through the use of permanent magnets, electromagnets, or the like. In another embodiment, the externally applied field includes an electric field. The electric field may be generated from an electric field generator, i.e., a system able to produce an electric field, for example, directed substantially at the channel or at the channel outlet, and/or directed proximate the fluidic stream exiting the channel outlet. Techniques for producing a suitable electric field are known to those of ordinary skill in the art. For example, an electric field may be produced by applying a voltage drop across electrodes positioned proximate the channel outlet and/or fluidic stream. The electrodes can be fashioned from any suitable electrode material, for example, as silver, gold, copper, carbon, platinum, copper, tungsten, tin, cadmium, nickel, indium tin oxide ("ITO"), etc., as is known to those of ordinary skill in the art. In some cases, transparent or substantially transparent electrodes may be used.

In some embodiments, the fluid and the liquid may be essentially immiscible, i.e., immiscible on a time scale of interest (e.g., the time it takes a fluidic droplet to be transported through a particular system or device). In certain cases, the droplets may each be substantially the same shape or size, as further described below. The fluid may also contain other species, for example, certain molecular species (e.g., as further discussed below), cells, particles, etc.

In one set of embodiments, electric charge may be created on a fluid surrounded by a liquid, which may cause the fluid to separate into individual droplets within the liquid. In some embodiments, the fluid and the liquid may be present in a channel, e.g., a microfluidic channel, or other constricted space that facilitates application of an electric field to the fluid (which may be "AC" or alternating current, "DC" or direct current etc.), for example, by limiting movement of the fluid with respect to the liquid. Thus, the fluid can be present as a series of individual charged and/or electrically inducible droplets within the liquid. In one embodiment, the electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc.

Electric charge may be created in the fluid within the liquid using any suitable technique, for example, by placing the fluid within an electric field (which may be AC, DC, etc.), and/or causing a reaction to occur that causes the fluid to have an electric charge, for example, a chemical reaction, an ionic reaction, a photocatalyzed reaction, etc. In one embodiment, the fluid is an electrical conductor. As used herein, a "conductor" is a material having a conductivity of at least about the conductivity of 18 megohm (MOhm or) water. The liquid surrounding the fluid may have a conductivity less than that of the fluid. For instance, the liquid may be an insulator, relative to the fluid, or at least a "leaky insulator," i.e., the liquid is able to at least partially electrically insulate the fluid for at least a short period of time. Those of ordinary skill in the art will be able to identify the conductivity of fluids. In one non-limiting embodiment, the fluid may be substantially hydrophilic, and the liquid surrounding the fluid may be substantially hydrophobic.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be manually separated from each other without cutting or breaking at least one of the components.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used. In certain embodiments, the electric field generator can be constructed and arranged (e.g., positioned) to create an electric field applicable to the fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric field intensities may be used, for example, at least about 2 V/micrometer, at least about 3 V/micrometer, at least about 5 V/micrometer, at least about 7 V/micrometer, or at least about 10 V/micrometer or more.

In some embodiments of the invention, systems and methods are provided for at least partially neutralizing an electric charge present on a fluidic droplet, for example, a fluidic droplet having an electric charge, as described above. For example, to at least partially neutralize the electric charge, the fluidic droplet may be passed through an electric field and/or brought near an electrode, e.g., using techniques such as those described herein. Upon exiting of the fluidic droplet from the electric field (i.e., such that the electric field no longer has a strength able to substantially affect the fluidic droplet), and/or other elimination of the electric field, the fluidic droplet may become electrically neutralized, and/or have a reduced electric charge.

In another embodiment, the fluidic droplets may not necessarily be given opposite electric charges (and, in some cases, may not be given any electric charge), and are fused through the use of dipoles induced in the fluidic droplets that causes the fluidic droplets to coalesce. The electric field used to induce dipoles may be an AC field, a DC field, etc.

In another set of embodiments, droplets of fluid can be created from a fluid surrounded by a liquid within a channel by altering the channel dimensions in a manner that is able to induce the fluid to form individual droplets. The channel may, for example, be a channel that expands relative to the direction of flow, e.g., such that the fluid does not adhere to the channel walls and forms individual droplets instead, or a channel that narrows relative to the direction of flow, e.g., such that the fluid is forced to coalesce into individual droplets. In other embodiments, internal obstructions may also be used to cause droplet formation to occur. For instance, baffles, ridges, posts, or the like may be used to disrupt liquid flow in a manner that causes the fluid to coalesce into fluidic droplets.

In some cases, the channel dimensions may be altered with respect to time (for example, mechanically or electromechanically, pneumatically, etc.) in such a manner as to cause the formation of individual fluidic droplets to occur. For example, the channel may be mechanically contracted ("squeezed") to cause droplet formation, or a fluid stream may be mechanically disrupted to cause droplet formation, for example, through the use of moving baffles, rotating blades, or the like.

Other examples of the production of droplets of fluid surrounded by a liquid are described in International Patent Application Serial No. PCT/US2004/010903, filed Apr. 9, 2004 by Link, et al. and International Patent Application Serial No. PCT/US03/20542, filed Jun. 30, 2003 by Stone, et al., published as WO 2004/002627 on Jan. 8, 2004, each incorporated herein by reference.

In some embodiments, the fluidic droplets may each be substantially the same shape and/or size. The shape and/or size can be determined, for example, by measuring the average diameter or other characteristic dimension of the droplets. The term "determining," as used herein, generally refers to the analysis or measurement of a species, for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasi-electric light scattering; polarimetry; refractometry; or turbidity measurements.

The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

In certain embodiments of the invention, the fluidic droplets may contain additional entities, for example, other chemical, biochemical, or biological entities (e.g., dissolved or suspended in the fluid), cells, particles, gases, molecules, or the like. In some cases, the droplets may each be substantially the same shape or size, as discussed above. In certain instances, the invention provides for the production of droplets consisting essentially of a substantially uniform number of entities of a species therein (i.e., molecules, cells, particles, etc.). For example, about 90%, about 93%, about 95%, about 97%, about 98%, or about 99%, or more of a plurality or series of droplets may each contain the same number of entities of a particular species. For instance, a substantial number of fluidic droplets produced, e.g., as described above, may each contain 1 entity, 2 entities, 3 entities, 4 entities, 5 entities, 7 entities, 10 entities, 15 entities, 20 entities, 25 entities, 30 entities, 40 entities, 50 entities, 60 entities, 70 entities, 80 entities, 90 entities, 100 entities, etc., where the entities are molecules or macromolecules, cells, particles, etc. In some cases, the droplets may each independently contain a range of entities, for example, less than 20 entities, less than 15 entities, less than 10 entities, less than 7 entities, less than 5 entities, or less than 3 entities in some cases. In one set of embodiments, in a liquid containing droplets of fluid, some of which contain a species of interest and some of which do not contain the species of interest, the droplets of fluid may be screened or sorted for those droplets of fluid containing the species as further described below (e.g., using fluorescence or other techniques such as those described above), and in some cases, the droplets may be screened or sorted for those droplets of fluid containing a particular number or range of entities of the species of interest, e.g., as previously described. Thus, in some cases, a plurality or series of fluidic droplets, some of which contain the species and some of which do not, may be enriched (or depleted) in the ratio of droplets that do contain the species, for example, by a factor of at least about 2, at least about 3, at least about 5, at least about 10, at least about 15, at least about 20, at least about 50, at least about 100, at least about 125, at least about 150, at least about 200, at least about 250, at least about 500, at least about 750, at least about 1000, at least about 2000, or at least about 5000 or more in some cases. In other cases, the enrichment (or depletion) may be in a ratio of at least about $10^4$, at least about $10^5$, at least about $10^6$, at least about $10^7$, at least about $10^8$, at least about $10^9$, at least about $10^{10}$, at least about $10^{11}$, at least about $10^{12}$, at least about $10^{13}$, at least about $10^{14}$, at least about $10^{15}$, or more. For example, a fluidic droplet containing a particular species may be selected from a library of fluidic droplets containing various species, where the library may have about $10^5$, about $10^6$, about $10^7$, about $10^8$, about $10^9$, about $10^{10}$, about $10^{11}$, about $10^{12}$, about $10^{13}$, about $10^{14}$, about $10^{15}$, or more items, for example, a DNA library, an RNA library, a protein library, a combinatorial chemistry library, etc. In certain embodiments, the droplets carrying the species may then be fused, reacted, or otherwise used or processed, etc., as further described below, for example, to initiate or determine a reaction.

A variety of definitions are now provided which will aid in understanding various aspects of the invention. Following, and interspersed with these definitions, is further disclosure that will more fully describe the invention. As noted, various aspects of the present invention relate to droplets of fluid surrounded by a liquid (e.g., suspended). The droplets may be of substantially the same shape and/or size, or of different shapes and/or sizes, depending on the particular application. As used herein, the term "fluid" generally refers to a substance that tends to flow and to conform to the outline of its container, i.e., a liquid, a gas, a viscoelastic fluid, etc. Typically, fluids are materials that are unable to withstand a static shear stress, and when a shear stress is applied, the fluid experiences a continuing and permanent distortion. The fluid may have any suitable viscosity that permits flow. If two or more fluids are present, each fluid may be independently selected among essentially any fluids (liquids, gases, and the like) by those of ordinary skill in the art, by considering the relationship between the fluids. The fluids may each be miscible or immiscible. For example, two fluids can be selected to be essentially immiscible within the time frame of formation of a stream of fluids, or within the time frame of reaction or interaction. Where the portions remain liquid for a significant period of time, then the fluids should be essentially immiscible. Where, after contact and/or formation, the dispersed portions are quickly hardened by polymerization or the like, the fluids need not be as immiscible. Those of ordinary skill in the art can select suitable miscible or immiscible fluids, using contact angle measurements or the like, to carry out the techniques of the invention.

As used herein, a first entity is "surrounded" by a second entity if a closed planar loop can be drawn around the first entity through only the second entity. A first entity is "completely surrounded" if closed loops going through only the second entity can be drawn around the first entity regardless of direction (orientation of the loop). In one embodiment, the first entity is a cell, for example, a cell suspended in media is surrounded by the media. In another embodiment, the first entity is a particle. In yet another embodiment, the first entity is a fluid. The second entity may also be a fluid in some cases (e.g., as in a suspension, an emulsion, etc.), for example, a hydrophilic liquid may be suspended in a hydrophobic liquid, a hydrophobic liquid may be suspended in a hydrophilic liquid, a gas bubble may be suspended in a liquid, etc. Typically, a hydrophobic liquid and a hydrophilic liquid are essentially immiscible with respect to each other, where the hydrophilic liquid has a greater affinity to water than does the hydrophobic liquid. Examples of hydrophilic liquids include, but are not limited to, water and other aqueous solutions comprising water, such as cell or biological media, salt solutions, etc., as well as other hydrophilic liquids such as ethanol. Examples of hydrophobic liquids include, but are not limited to, oils such as hydrocarbons, silicone oils, mineral oils, fluorocarbon oils, organic solvents etc. Other examples of suitable fluids have been previously described.

Similarly, a "droplet," as used herein, is an isolated portion of a first fluid that is completely surrounded by a second fluid. It is to be noted that a droplet is not necessarily spherical, but may assume other shapes as well, for example, depending on the external environment. In one embodiment, the droplet has a minimum cross-sectional dimension that is substantially equal to the largest dimension of the channel perpendicular to fluid flow in which the droplet is located.

As mentioned, in some, but not all embodiments, the systems and methods described herein may include one or more microfluidic components, for example, one or more microfluidic channels. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria. The "cross-sectional dimension" of the channel is measured perpendicular to the direction of fluid flow within the channel. Thus, some or all of the fluid channels in microfluidic embodiments of the invention may have maximum cross-sectional dimensions less than 2 mm, and in certain cases, less than 1 mm. In one set of embodiments, all fluid channels containing embodiments of the invention are microfluidic or have a largest cross sectional dimension of no more than 2 mm or 1 mm. In certain embodiments, the fluid channels may be formed in part by a single component (e.g. an etched substrate or molded unit). Of course, larger channels, tubes, chambers, reservoirs, etc. can be used to store fluids and/or deliver fluids to various components or systems of the invention. In one set of embodiments, the maximum cross-sectional dimension of the channel(s) containing embodiments of the invention is less than 500 microns, less than 200 microns, less than 100 microns, less than 50 microns, or less than 25 microns.

A "channel," as used herein, means a feature on or in an article (substrate) that at least partially directs flow of a fluid. The channel can have any cross-sectional shape (circular, oval, triangular, irregular, square or rectangular, or the like) and can be covered or uncovered. In embodiments where it is completely covered, at least one portion of the channel can have a cross-section that is completely enclosed, or the entire channel may be completely enclosed along its entire length with the exception of its inlet(s) and/or outlet(s). A channel may also have an aspect ratio (length to average cross sectional dimension) of at least 2:1, more typically at least 3:1, 5:1, 10:1, 15:1, 20:1, or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to fluid flow of less than about 5 mm or 2 mm, or less than about 1 mm, or less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, positioned to intersect with each other, etc.

In one set of embodiments, the fluidic droplets may contain cells or other entities, such as proteins, viruses, macromolecules, particles, etc. As used herein, a "cell" is given its ordinary meaning as used in biology. The cell may be any cell or cell type. For example, the cell may be a bacterium or other single-cell organism, a plant cell, or an animal cell. If the cell is a single-cell organism, then the cell may be, for example, a protozoan, a trypanosome, an amoeba, a yeast cell, algae, etc. If the cell is an animal cell, the cell may be, for example, an invertebrate cell (e.g., a cell from a fruit fly), a fish cell (e.g., a zebrafish cell), an amphibian cell (e.g., a frog cell), a reptile cell, a bird cell, or a mammalian cell such as a primate cell, a bovine cell, a horse cell, a porcine cell, a goat cell, a dog cell, a cat cell, or a cell from a rodent such as a rat or a mouse. If the cell is from a multicellular organism, the cell may be from any part of the organism. For instance, if the cell is from an animal, the cell may be a cardiac cell, a fibroblast, a keratinocyte, a heptaocyte, a chondracyte, a neural cell, a osteocyte, a muscle cell, a blood cell, an endothelial cell, an immune cell (e.g., a T-cell, a B-cell, a macrophage, a neutrophil, a basophil, a mast cell, an eosinophil), a stem cell, etc. In some cases, the cell may be a genetically engineered cell. In certain embodiments, the cell may be a Chinese hamster ovarian ("CHO") cell or a 3T3 cell.

A variety of materials and methods, according to certain aspects of the invention, can be used to form any of the above-described components of the systems and devices of the invention. In some cases, the various materials selected lend themselves to various methods. For example, various components of the invention can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, Scientific American, 248:44-55, 1983 (Angell, et al). In one embodiment, at least a portion of the fluidic system is formed of silicon by etching features in a silicon chip. Technologies for precise and efficient fabrication of various fluidic systems and devices of the invention from silicon are known. In another embodiment, various components of the systems and devices of the invention can be formed of a polymer, for example, an elastomeric polymer such as polydimethylsiloxane ("PDMS"), polytetrafluoroethylene ("PTFE" or Teflon®), or the like.

Different components can be fabricated of different materials. For example, a base portion including a bottom wall and side walls can be fabricated from an opaque material such as silicon or PDMS, and a top portion can be fabricated from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be fabricated as illustrated, with interior channel walls coated with another material. Material used to fabricate various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

In one embodiment, various components of the invention are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred in one set of embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," Anal. Chem., 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one embodiment, a bottom wall is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

The following documents are incorporated herein by reference: U.S. patent application Ser. No. 11/360,845, filed Feb. 23, 2006, entitled "Electronic Control of Fluidic Species," by Link, et al., published as U.S. Patent Application Publication No. 2007/0003442 on Jan. 4, 2007; U.S. patent application Ser. No. 08/131,841, filed Oct. 4, 1993, entitled "Formation of Microstamped Patterns on Surfaces and Derivative Articles," by Kumar, et al., now U.S. Pat. No. 5,512,131, issued Apr. 30, 1996; priority to International Patent Application No. PCT/US96/03073, filed Mar. 1, 1996, entitled "Microcontact Printing on Surfaces and Derivative Articles," by Whitesides, et al., published as WO 96/29629 on Jun. 26, 1996; U.S. patent application Ser. No. 09/004,583, filed Jan. 8, 1998, entitled "Method of Forming Articles Including Waveguides via Capillary Micromolding and Microtransfer Molding," by Kim, et al., now U.S. Pat. No. 6,355,198, issued Mar. 12, 2002; International Patent Application No. PCT/US01/16973, filed May 25, 2001, entitled "Microfluidic Systems including Three-Dimensionally Arrayed Channel Networks," by Anderson, et al., published as WO 01/89787 on Nov. 29, 2001; U.S. Provisional Patent Application Ser. No. 60/392,195, filed Jun. 28, 2002, entitled "Multiphase Microfluidic System and Method," by Stone, et al.; U.S. Provisional Patent Application Ser. No. 60/424,042, filed Nov. 5, 2002, entitled "Method and Apparatus for Fluid Dispersion," by Link, et al.; U.S. Provisional Patent Application Ser. No. 60/461,954, filed Apr. 10, 2003, entitled "Formation and Control of Fluidic Species," by Link, et al.; International Patent Application No. PCT/US03/20542, filed Jun. 30, 2003, entitled "Method and Apparatus for Fluid Dispersion," by Stone, et al., published as WO 2004/002627 on Jan. 8, 2004; U.S. Provisional Patent Application Ser. No. 60/498,091, filed Aug. 27, 2003, entitled "Electronic Control of Fluidic Species," by Link, et al.; International Patent Application No. PCT/US2004/010903, filed Apr. 9, 2004, entitled "Formation and Control of Fluidic Species," by Link, et al., published as WO 2004/091763 on Oct. 28, 2004; International Patent Application No. PCT/US2004/027912, filed Aug. 27, 2004, entitled "Electronic Control of Fluidic Species," by Link, et al., published as WO 2005/021151 on Mar. 10, 2005; U.S. patent application Ser. No. 11/024,228, filed Dec. 28, 2004, entitled "Method and Apparatus for Fluid Dispersion," by Stone, et al., published as U.S. Patent Application Publication No. 2005-0172476 on Aug. 11, 2005; U.S. Provisional Patent Application Ser. No. 60/659,045, filed Mar. 4, 2005, entitled "Method and Apparatus for Forming Multiple Emulsions," by Weitz, et al.; U.S. Provisional Patent Application Ser. No. 60/659,046, filed Mar. 4, 2005, entitled "Systems and Methods of Forming Particles," by Garstecki, et al.; and U.S. patent application Ser. No. 11/246,911, filed Oct. 7, 2005, entitled "Formation and Control of Fluidic Species," by Link, et al.

In addition, U.S. Provisional Patent Application Ser. No. 61/376,137, filed Aug. 23, 2010, entitled "Acoustic Waves in Microfluidics," by Weitz, et al., is incorporated herein by reference.

The following examples are intended to illustrate certain embodiments of the present invention, but do not exemplify the full scope of the invention.

EXAMPLE 1

This example describes a microfluidic cell sorter which operates in continuous flow at high sorting rates. The device is based on a surface acoustic wave cell-sorting scheme and combines many advantages of fluorescence activated cell sorting (FACS) and fluorescence activated droplet sorting (FADS) in microfluidic channels. It is fully integrated on a PDMS device, and allows fast electronic control of cell diversion. Cells were directed by acoustic streaming excited by a surface acoustic wave which deflects the fluid independently of the contrast in material properties of deflected objects and the continuous phase; thus the device underlying principle works without additional enhancement of sorting by prior labeling of the cells with responsive markers such as magnetic or polarizable beads. Single cells were sorted directly from bulk media at rates as fast as several kHz (thousands of droplets per second) without prior encapsulation into liquid droplet compartments as in traditional FACS. These experiments showed successful sorting of HaCaT cells (human keratinocytes), fibroblasts from mice and MV3 melanoma cells. The low shear forces of this sorting method ensure that cells survive after sorting.

This example illustrates the advantage of fast cell sorting of FACS in the kHz regime with the advantages of microfluidic technology. The device operated in continuous flow without enclosing cells in droplets or labeling them with responsive beads prior to separation. A low cost disposable microfluidic polydimethylsiloxane (PDMS) device was used with a tiny dead volume. The device could handle total process volumes as small as ~100 microliters. The sorting was fully electronically controlled and integrated on the microfluidic chip. Because hydrodynamic flow was actuated in bulk, the shear stress on the cells is minimized and cells remain viable after sorting.

The physical principle of the technique is based on an effect called "acoustic streaming." Surface acoustic waves (SAW) were used to drive microflows in the PDMS channels. As long as the SAW propagates on the surface of the substrate, it is barely damped. However, when the substrate is covered with water the wave irradiates energy into the liquid which gives rise to internal streaming of the fluid. The effect has been utilized to actuate droplets on open surfaces and in closed channels and to enhance mixing. This streaming effect differs significantly from another commonly used technique which employs standing surface acoustic waves (SSAW) which can be used to align and wash particles. However, the underlying physical principle is different: In SSAW, a stationary standing wave is built up and objects are driven to positions of larger or smaller wave amplitude according to their compressibility contrast with respect to the suspending medium. This force is often termed as acoustic radiation force and is induced by an ultrasonic standing wave field. Acoustic radiation force acting on an interface between two liquids with different densities can also be used to actuate the heterogeneous fluid itself. By contrast, in this device, the homogeneous continuous fluid including the objects was actuated, and no contrast in compressibility, dielectric constant or density was required.

The sorting device presented in this example directed cells by acoustic streaming induced by a surface acoustic wave on a piezoelectric substrate. The surface acoustic wave was excited by an interdigitated transducer (IDT). The IDT had two gold electrodes deposited onto the piezoelectric substrate, each with a comb-like interdigitated-finger structure. The operating frequency of the IDT was determined by the ratio of the sound velocity in the substrate to twice the finger spacing. The IDT had a tapered shape with a decreasing finger repeat distance varying from 23 to 28 micrometers. This provided a narrow wave path width for sound wave propagating on the substrate because the finger spacing only obeys the resonance condition at one position. The frequency was varied between 140 MHz and 150 MHz, which corresponded to a finger spacing of 25.4 micrometers to 27.3 micrometers. The gold electrodes were produced by vapor deposition and standard lithography. The anisotropic piezoelectric substrate was a Y-cut $LiNbO_3$ with the crystal axis rotated around the X-axis by 128° (128° Y-Cut). The fingers of the IDT were aligned perpendicular to the X-axis and the alternating RF frequency therefore excited a Rayleigh wave propagating in the direction of the X-axis. To apply high frequency voltage, a GHz-signal generator (Wavetek, Model 3010) was used, and the signal subsequently amplified to a power of ~30 dBm.

To assemble the microfluidic hybrid device, both the PDMS mold and the piezo-substrate were treated in ozone plasma and assembled on top of each other under a microscope. The enclosed PDMS channel with a height of 50 micrometers and three inlets was fabricated using soft lithography. The fluid in the main channel, which contained the cells, was hydrodynamically focused by the fluid from the two side inlets to align the cells horizontally, and the cells were subsequently sorted in one of the two outlet channels. The IDT was positioned directly beside the channel and cells flowed into the collect or waste channel, depending on the actuation state of the IDT as shown in FIG. 1. The bonded PDMS-SAW hybrid device was mounted on the stage of an inverted fluorescence microscope and imaged by a fast camera (Photron, Fastcam 1024 PCI).

FIG. 1 shows schematic illustrations and corresponding phase contrast micrographs of the surface-acoustic-wave-actuated PDMS hybrid chip for cell sorting. These figures show that the main channel was hydrodynamically focused by adjusting the flows through two side channels. Without applying a surface acoustic wave, the jet of the main channel moved into the left outlet channel due to its lower hydrodynamic resistance. Schematic illustrations and phase contrast micrographs are shown in FIGS. 1A and 1C ("OFF"). When switching on the SAW, acoustic streaming was induced and deflected the focusing stream into the right channel outlet in FIGS. 1B and 1D ("ON"). Because cells were only in the focused region of the flow, they could be directed into a desired channel. The dark and the light region in the schematic illustration and the micrograph respectively were the areas of contact of PDMS mold and piezo-substrate.

The usefulness of this device for cell sorting was demonstrated with three different cell types: HaCaT cells (humane keratinocytes, Biochrom AG, Berlin), murine fibroblasts L929 cells (obtained from S. Thalhammer, Munich) and MV3 melanoma cells (obtained from S. Schneider, Munster). The HaCaT cells and the murine fibroblasts were maintained in RPMI medium (Biochrom AG), the MV3-cells in MEM medium (PAA). All media were supplemented with 10% fetal bovine serum (PAA) and 1% streptavidin/penicillin. Confluent cells were harvested with Trypsin/EDTA. For sorting experiments, the cells were resuspended in a 0.85% (w/v) NaCl solution, buffered with Hepes (30 mM) containing 1% (w/v) BSA and 14% OptiPrep (Sigma-Aldrich) density gradient medium to increase buoyancy for density matching. The sheath buffer was PBS (pH 7.4) only.

The SAW deflected the flow only in a small region between $y_{ON}$ and $y_{OFF}$ as highlighted in FIG. 2. The action of the surface acoustic wave input on the acoustic streaming was instantaneous on a millisecond-time scale, but because the shaded region of SAW coupling and the sorting junction at the origin of the x-y coordinate system in FIG. 2 do not coincide its effect on sorting was delayed by the time that it takes for the deflected fluid flow to reach the sorting junction.

Figure 2B:
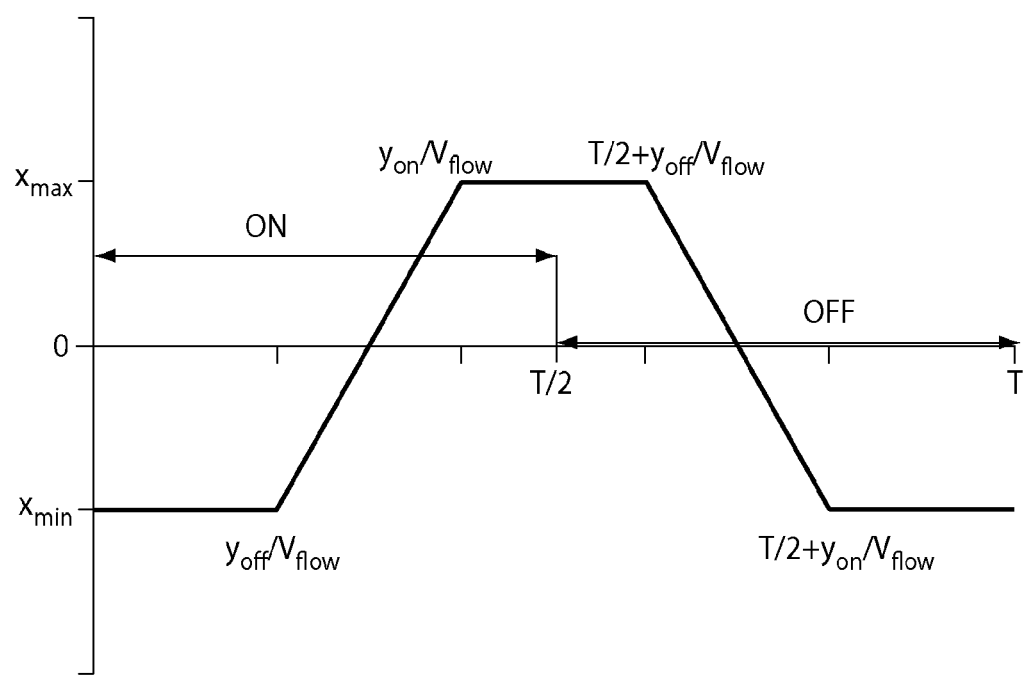

To illustrate the sorting principle and correlate the input signal (power on/off) of the SAW to the output signal, which is the deflection of the focused jet, a square wave input is considered as shown in FIG. 2B. The period T of the square wave is given by the square wave modulation frequency $f_{IDT}$ of the interdigital transducer $T=1/f_{IDT}$ and determines the sorting rate. In this experiment, this frequency $f_{IDT}$ was varied between 100 Hz and 2 kHz.

Such a signal causes an x-deflection at position y=0 as shown in the right schematic plot: the onset of SAW pulse is at time t=0, and has no immediate x-deflection, $x=x_{min}$ (jet flows in left outlet channel). Instead, the action of the SAW causes deflection at this position only after a delay of $t_{delay}=y_{off}/v_{flow}$, with flow velocity $v_{flow}$, because the diversion in the flow has to travel downstream. This is followed by a linear increase in deflection up to the maximum at $t=y_{on}/v_{flow}$. At that time a particle with initial position $y=y_{on}$ at t=0 passes the branch at y=0. This maximal deflection $x=x_{max}$ lasts until the SAW power is switched off again at t=T/2, whereupon the flow follows the reverse characteristics of the deflection profile. The maximum and minimum deflections can be controlled by the flow of side channels and the SAW power, while the flow velocity $v_{flow}$ can be adjusted by the inlet flow rates.

FIG. 2A shows a micrograph of a deflected hydrodynamically focused jet, and FIG. 2B shows a schematic of the time dependence of jet deflection in the microchannel caused by switching a square wave "ON" and "OFF." The square wave is the input signal (square wave modulation of SAW) and the other line corresponds to the output signal (fluid jet deflection). The origin of the x-y coordinates is set to be at the branch of the waste and collect channels. The y-direction is the flow direction of the liquid flow and the x-direction is the direction of deflection due to an applied SAW. The region where the SAW is acting on the jet is shaded in FIG. 2A.

Periodically alternating the amplitude of the surface acoustic wave caused the focused jet to deflect with the same frequency as the modulation frequency of the exciting SAW.

A cell moving from the main channel is aligned within this jet and follows the flow downstream as shown in FIG. 3. The position of the jet prior to the sorting experiment could be adjusted by controlling the pressure of the sheath flows with the SAW off. This procedure was important in some cases to the sorting ratio of cells in the left and right channel for periodically oscillating excitation. For instance, if one intends a 1:1 sorting in both outlets, then $x_{min}$ can be set to be equal to $-x_{max}$ (see also FIG. 2).

The sorting efficiency was evaluated by the number of cells sorted into the collect and waste channel respectively. A periodically oscillating square wave signal depending on time was applied to the IDT and its frequency $f_{IDT}$ varied from 100 Hz to 2 kHz. Here, one would expect cells to be periodically sorted into the collect channel when the SAW is switched on and into the waste channel when the SAW is switched off. The time dependence was characterized by the phase angle. The phase angle is the time since the last switch off of the SAW divided by the period T. For each frequency, the number of cells falling into one of the channels was counted as a function of the corresponding phase angle φ.

Experimentally, it was found that for one phase angle interval all cells were directed in the collect channel, while for another interval all cells entered the waste channel without exception (i.e., 100% sorting efficiency). The length of these intervals was denoted by $\phi_{collect}$ and $\phi_{waste}$, respectively. In between $\phi_{collect}$ and $\phi_{waste}$ were intervals where cells entered both the collect and waste channel at the same phase angle. These transient intervals where sorting was ambiguous was defined by $\phi_{ON-OFF}$ and $\phi_{OFF-ON}$. It was found that the length of these transient intervals increased with sorting frequency while the lengths of $\phi_{collect}$ and $\phi_{waste}$ decreased. At a critical sorting frequency, the transient intervals expanded over the complete phase angle range (sorting efficiency<100%).

A typical experiment at 1 kHz oscillation frequency is shown in FIG. 4, together with a list summarizing all of the experiments with different cell types and frequencies. Hence, an integrated cell sorter with an automated detector should be operated below this critical frequency, at least in some cases. The width of the transient intervals also yielded an estimation of the critical sorting frequency. The width of the transient interval in FIG. 4 was ~3/12 f, thus the critical frequency in this particular example was estimated to be 4 kHz. At this frequency, the transient interval was expected to expand over all phase angles. Thus, a sorting rate of 2 kHz was achieved experimentally with 100% efficiency using this particular configuration.

The inherent gentleness of this method was demonstrated with a cell viability test. From a stock solution of the fluorophore Calcein AM in dimethyl sulfoxide (DMSO, 5 mg/ml), 2 microliters were added to a 1 ml cell suspension. Calcein AM is retained in cells that have intact membranes and gives rise to a fluorescent signal; however, it does not label dead cells, and is rapidly lost under conditions that cause cell lysis. This property allows the viability of the cells which have passed through the SAW sorting device to be evaluated. Among the cells which have passed the sorting device, 93% viable cells were detected as compared to 97% viability of reference sample of murine fibroblasts which have not passed through the device. For the HaCat cells, 94% of the cells passing the sorter were viable, as compared to a control reference of 97% viability. This confirms the low shear forces on the cells due to the flow induced by the SAW device.

Figure 3A:
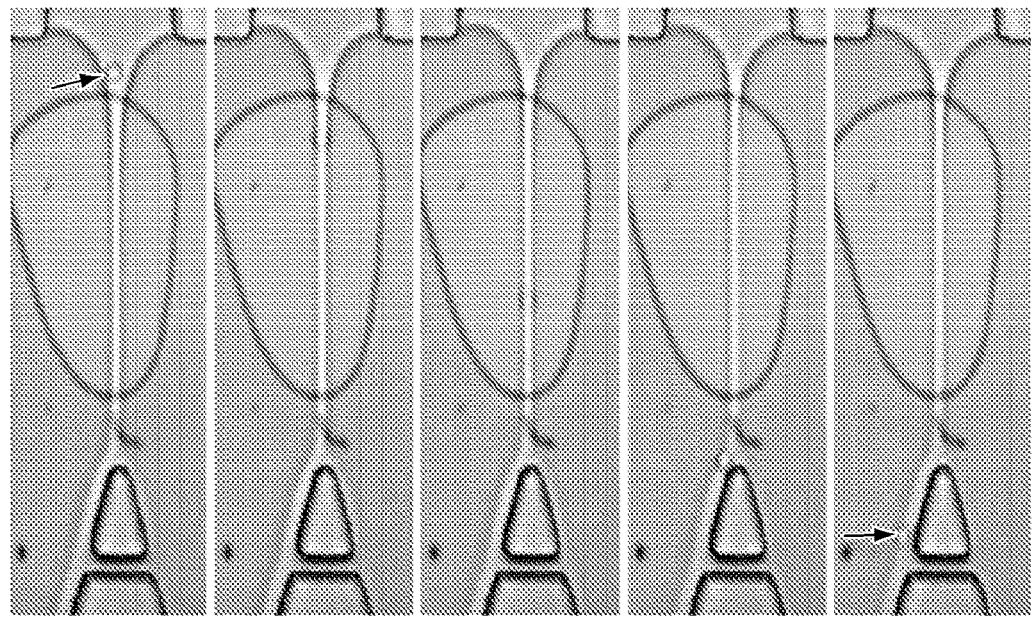
FIGS. 3A-3C illustrate the sorting of droplets in accordance with various other embodiments of the invention.
Figure 3B:
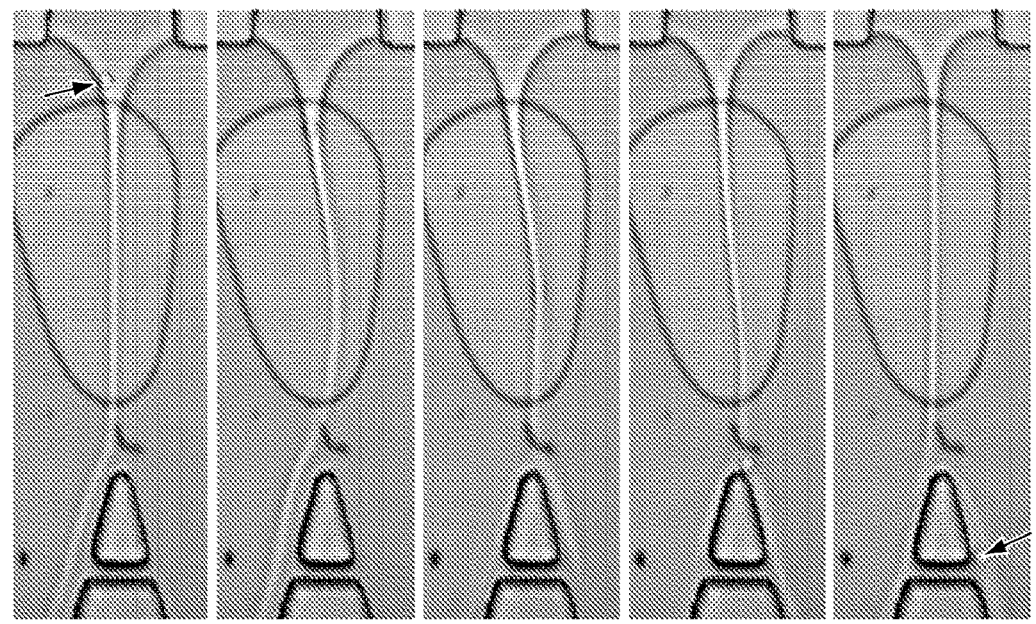
Figure 3C:
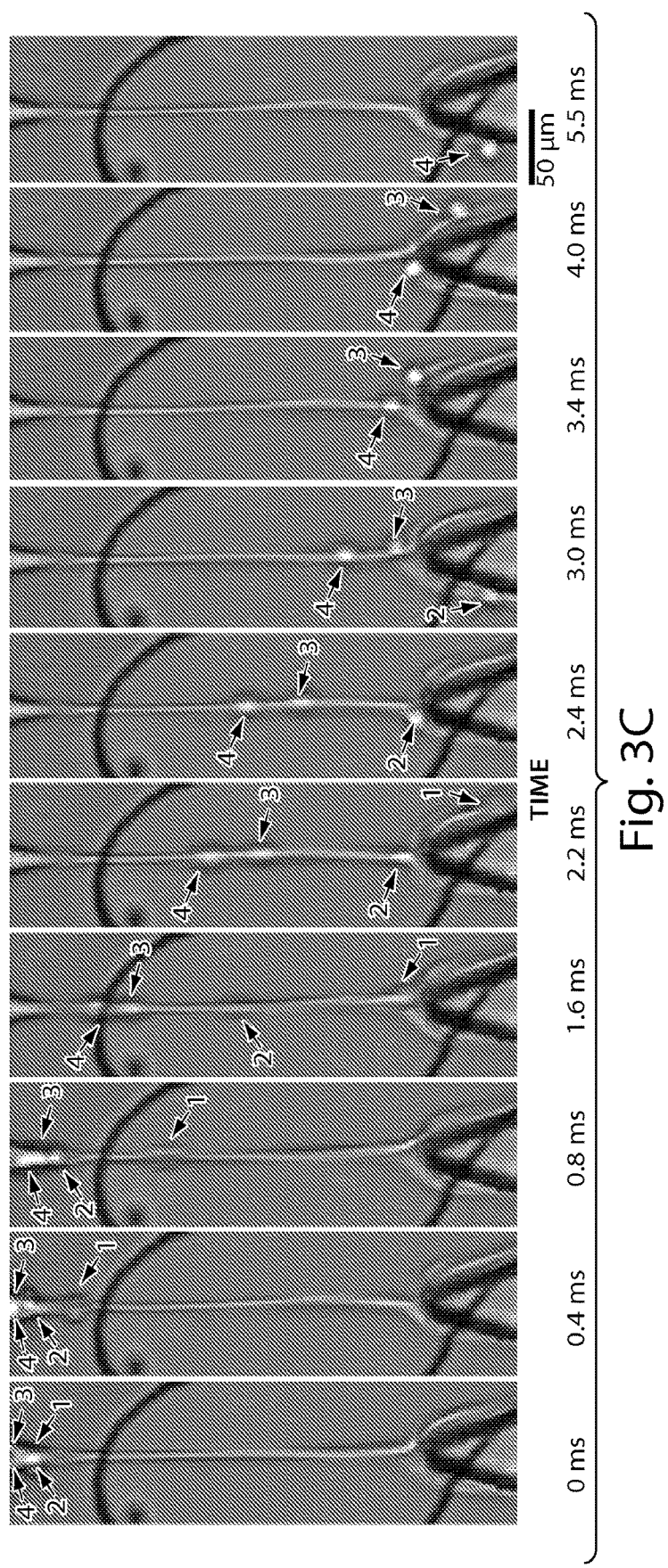

FIG. 3 illustrates cell sorting in two outlets upon application of a periodically oscillating SAW amplitude. FIG. 3A shows a cell entering the sorting region moves through the left channel if the SAW is switched off (default channel). FIG. 3B shows that after application of an electrical voltage to the IDT, the excited SAW bends the jet and diverts the cells into the right collection channel. The micrographs were taken at time intervals of 2 ms. FIG. 3C shows micrographs of MV3 cells sorted at 1 kHz. Several cells entered the flow focused area of the device from the top, in very close proximity, with three cells in contact. However, the cells were separated as the flow field of the hydrodynamic cell focused region was accelerated, and successively moved through different outlet channels. The distance attained between the cells was sufficient to alternately sort them at high frequency into the right and left outlet.

Figure 4A:
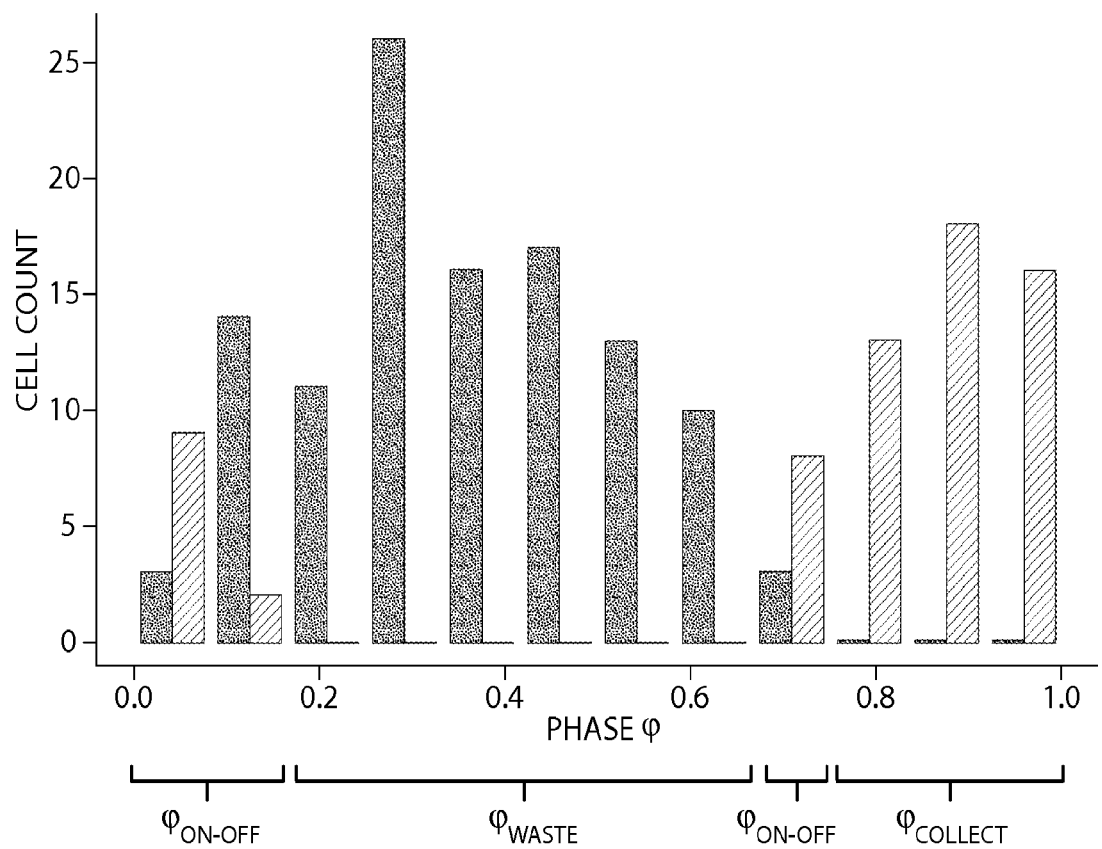

FIG. 4A shows the sorting efficiency of the acoustic sorter operating at 2 kHz sorting frequency (2 times oscillation frequency), using a cell count histogram. The cell counts were summarized over a small interval (1/12 $f_{IDT}$) and displayed as bars. Cells deflected in the collect channel (right bars) and the default channel (left bars, waste) when the SAW was applied are shown. Note that for phases within the intervals denoted as $\phi_{collect}$ and $\phi_{waste}$, all collected cells entered the respective channel without exception (100% efficiency). Only at small transient regions close to φ=0 and φ=0.65 were cells found within both channels. The width of the intervals $\phi_{collect}$ and $\phi_{waste}$ differed because the cell-transporting jet was not optimally adjusted for $x_{min}=-x_{max}$ (see also discussion above with respect to FIG. 3).

FIG. 4B is a table showing sorting efficiency dependence on sorting rate for different cell types. For lower frequencies, sorting efficiency was 100%, and all cells within the respective phase interval $\phi_{collect}$ and $\phi_{waste}$ were collected in the waste or collect channel. At higher frequencies, sorting was imperfect (lower than 100%), and no intervals $\phi_{collect}$ and $\phi_{waste}$ for perfect sorting could be defined. Here, the phase range was divided into only two intervals $\phi_{collect}$ and $\phi_{waste}$, and the transient intervals $\phi_{ON-OFF}$ and $\phi_{OFF-ON}$ (values are in brackets in the table) were neglected. The collect and waste efficiency were defined by the ratio of correctly sorted cells to the total number of cells falling into the corresponding interval. The highest 100% efficient sorting rate was found for fibroblasts to be 2 kHz.

In summary, this example shows a sorting scheme operating at high sorting rates of several kHz and demonstrate sorting of diverse types of cells including HaCaT cells, fibroblasts from mouse and MV3 melanoma cells. The gentleness of this method was demonstrated with a cell viability test. Due to the low dead volume, as little as 100 ml cell suspension may be sufficient. The SAW hybrid device is particularly useful when only small sample volumes may be available and/or when a high viability of sorted cells is desired (although the device may be used in other applications as well, of course). Furthermore, because the sorting operates in continuous flow, subsequent culturing of cells can be easily accomplished. The sorting device was fully assembled on a microfluidic substrate in this example and could be integrated into a more complex designs in some cases, such as with repeated sorting steps or other functional modules. Its low cost and disposability makes it useful for analysis in research as well as diagnostics.

EXAMPLE 2

Pumps are among the key components to actuate as well as control flow in microfluidic systems. There are a multitude of pumps that have been developed, exploiting various physical effects. Among these are pumps using electrophoretic or dielectrophoretic forces, capillary, magnetic forces, or mechanical techniques creating hydrodynamic pressure gradients to drive fluid flow. This example presents a pumping technique based on an acoustic streaming effect. This method shows tubeless fluid control without any external fluid connection, and pumping at high flow rates. The actuation principle used here is based on a SAW-induced counterflow mechanism and the effect of nebulization anisotropy, and relies on the droplet dynamics at the air-liquid interface.

Using this counterflow effect where SAW propagation and fluid actuation are oppositely directed, fluid was drawn from a reservoir into a channel and moved to a position in the array. The actuation principle of acoustic streaming was independent of pH or electrolyte concentration, and used low voltages, which may be important when pumping biological samples and to avoid electrochemical effects. Moreover, the method allowed the continuous actuation of non-stationary fluid flow with relatively fast response times. This may important for certain applications, for instance to, experimentally mimic the pulsed beat of blood flow through vessels.

Figure 5A:
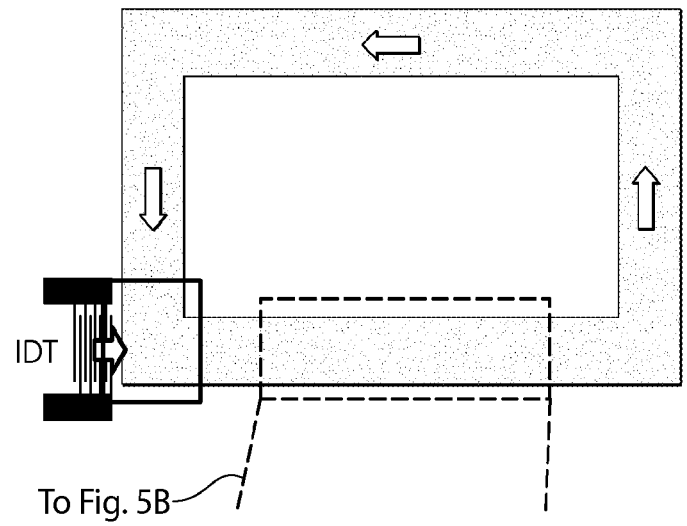
FIGS. 5A-5D illustrate acoustic waves in microfluidic channels, in still other embodiments of the invention.

These experiments used PDMS soft lithography and full integration of fluidic pump on a chip or substrate. Soft lithography using the elastomer polydimethysiloxane (PDMS) allowed fabrication of simple and low cost complex microfluidic channel structures in the substrate. The device pumped the fluid in a circle in a closed PDMS channel using acoustic streaming excited by an interdigital transducer (IDT) as shown in the schematic of FIG. 5A. The IDT comprised two gold electrodes on a piezoelectric substrate, each having a comb-like structure, which interdigitated at a fixed finger repeat distance. The ratio of the sound velocity in the substrate to twice the finger distance defined the operating frequency of the IDT. The IDT presented here had a finger spacing of about 13 micrometers and an operating frequency of 142 MHz. Gold electrodes were used in the IDT, and were produced by vapor deposition and standard lithography. The anisotropic piezoelectric substrate was a Y-cut of $LiNbO_3$, with the crystal axis rotated around the X-axis by 128° (128° Y-Cut). The fingers of the IDT were aligned perpendicular to the X-axis and the alternating RF frequency, therefore exciting a Rayleigh wave propagating in the direction of the X-axis. A fast alternating electric RF-field generated an oscillating displacement with an amplitude in the nm-range, which propagated at the velocity of sound on the surface of the piezoelectric substrate. To apply high frequency voltage, a GHz-signal generator (Rohde Schwarz, SML01) was used and the signal subsequently amplified. To complement the device, a microfluidic PDMS channel was assembled and sealed onto a cover slip through covalent bonding after ozone plasma treatment and carefully placed on top of the piezoelectric substrate using water as a contact liquid.

FIG. 5A shows a schematic of the hybrid PDMS-SAW chip as seen from above. The basic channel (width of 1 mm, height of 0.75 mm, loop circumference of 42 mm) was formed from a closed rectangular PDMS channel and was bonded onto a glass substrate. The IDT was positioned below the channel and pumped the fluid around the closed channel without inlets or outlets (arrows indicating flow direction). The IDT had 42 fingers, and an aperture of 624 micrometers and a length of 1233 micrometers. It was positioned in parallel to the fluid channel at the PDMS-fluid boundary.

Figure 5B:
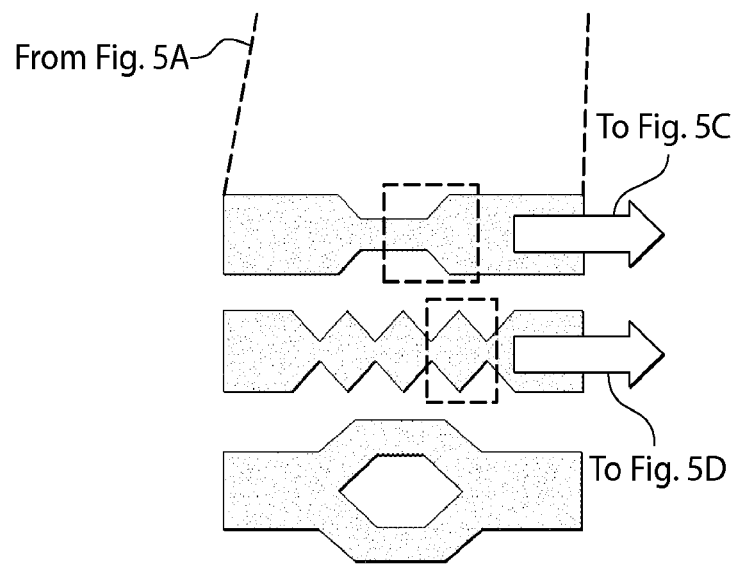
Figure 5C:
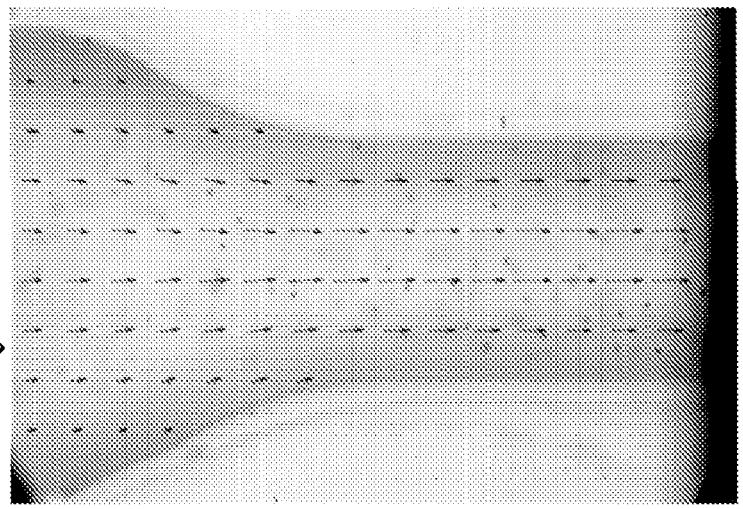
Figure 5D:
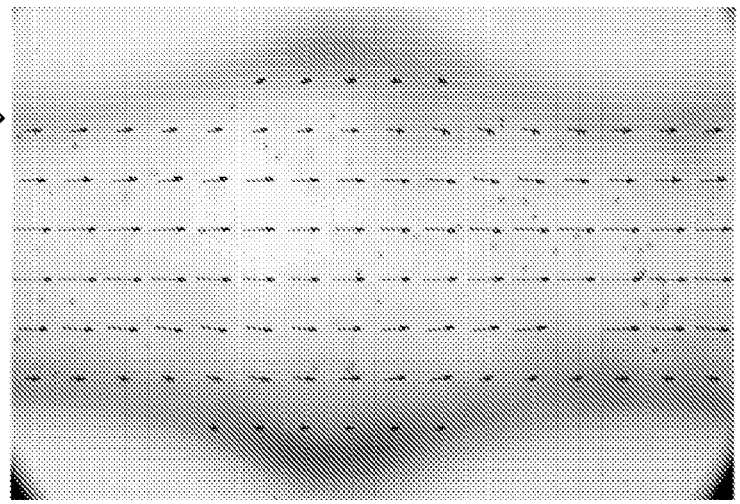

Enclosed by a dotted line is the region where the surface acoustic waves were applied to the fluid. A close-up of the coupling is shown in FIG. 6. Different channel designs were also tested, as indicated by the channel sections in FIG. 5B, including a narrowing nozzle-like channel, an oscillating zig-zag channel and a bifurcated channel. FIGS. 5C and 5D are micrographs of the different channels, and superposed with the experimentally measured flow velocity vectors (arrows) as obtained from particle tracking with focus in the symmetry plane, i.e., in the middle of the channel.

Figure 6A:
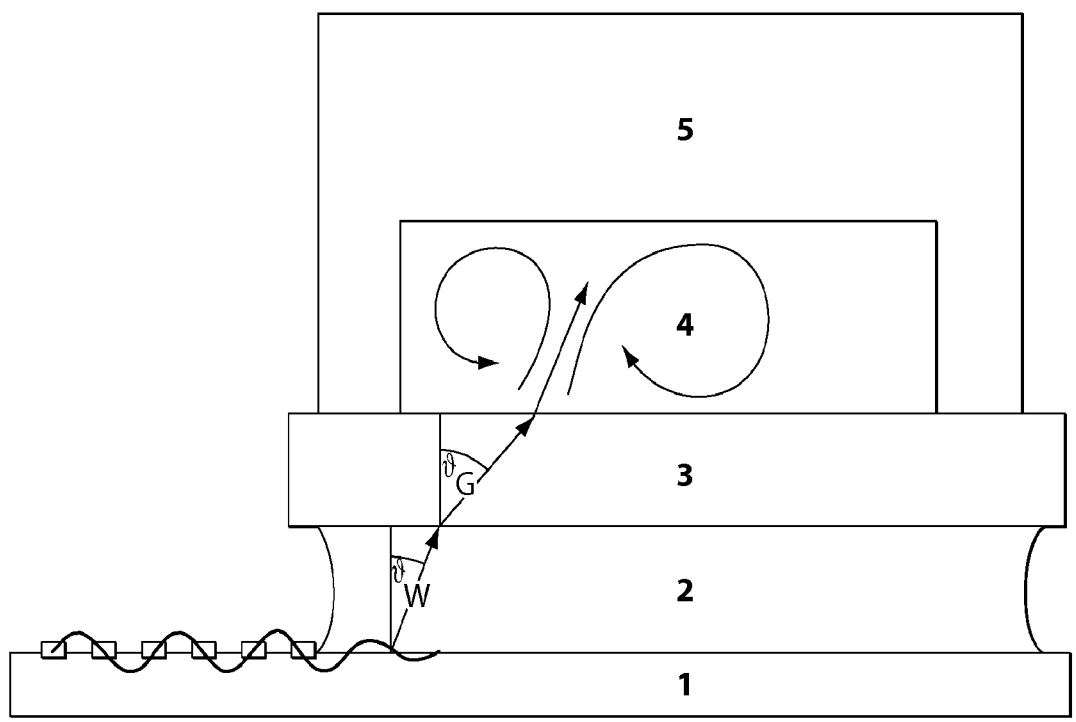
FIGS. 6A-6B illustrate acoustic wave coupling in accordance with another set of embodiments.

When a microfluidic channel was placed on top of the substrate, the Rayleigh wave generated an acoustic wave which coupled through the intermediate water layer and the glass bottom of the channel into the fluid, transferring momentum along the direction of propagation and ultimately inducing fluid streaming, as illustrated in FIG. 6A.

FIG. 6A shows a side view sketch of the path of the acoustic wave coupling into the channel, e.g., via a coupling region. In this figure, a surface acoustic wave is excited by the IDT and travels along a lithium niobate substrate (1). It is refracted as a longitudinal wave into the water (2) at a Rayleigh angle ($\theta_w$) of 21.8° while the surface wave on the substrate is attenuated on a characteristic length scale of 325 micrometers. The longitudinal acoustic wave passes through the 150 micrometer thick water layer and is subsequently refracted as a transversal wave into the glass coverslide at a Rayleigh angle ($\theta_G$) of 54.4°. At the top of the glass slide, the wave is refracted again, enters the water-filled channel (4) and transfers momentum to the liquid, causing acoustic streaming as indicated, before it couples into the PDMS layer on top where it is further dampened.

Figure 6B:
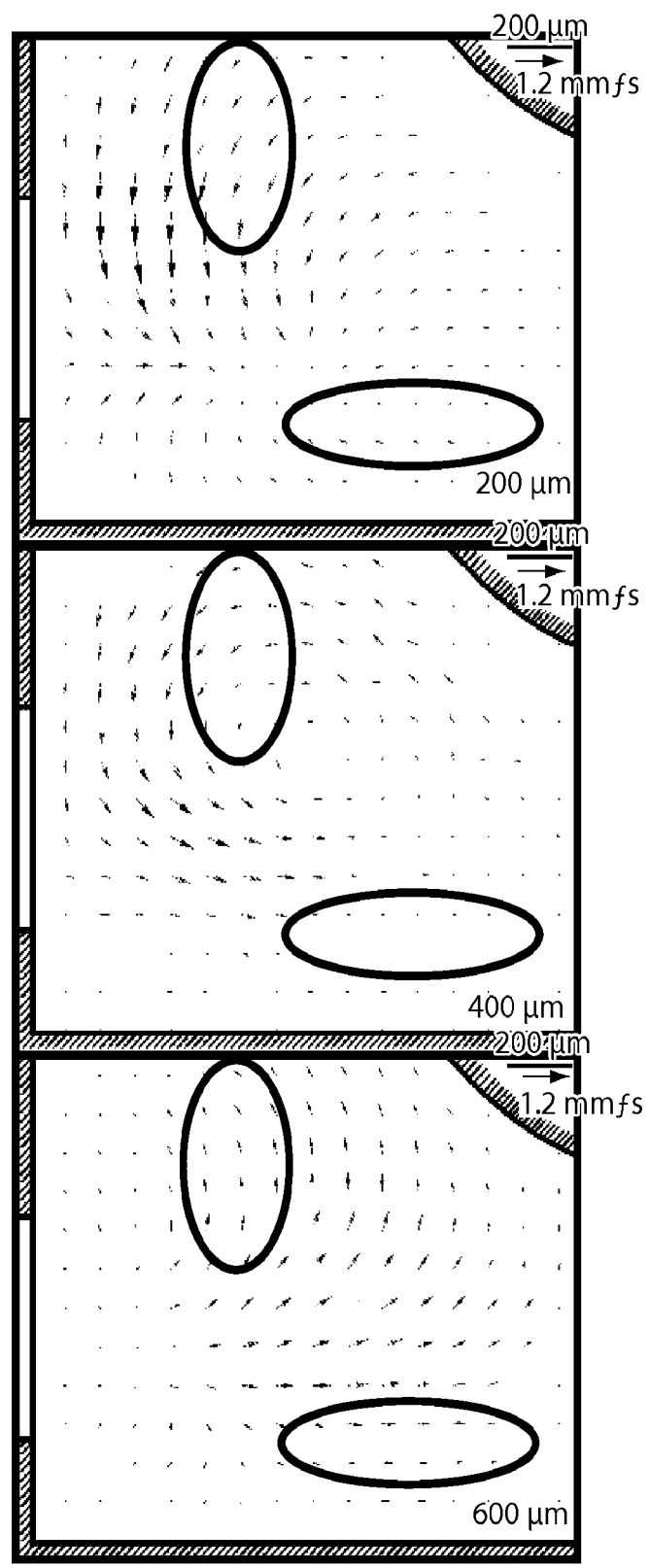

In the actuation region, the SAW created several flow vortices that have been observed using particle image velocimetry as shown in FIG. 6B. This figure shows flow profiles at different z planes at the SAW actuation region (indicated in FIG. 5A as a square). The rectangle on the left of this figure indicates the position of the IDT. The horizontal vortex (in the z plane) generated by the acoustic wave is visible, and in addition, two vertical vortices are present and denoted by ellipses. They can be inferred when comparing the flow velocities on the top and bottom planes. The actuation power was 12 dBm.

This complex flow pattern created a pressure difference that drives the flow along the channel as shown in FIG. 5. The flow velocity could be controlled electronically by the SAW power and may work without any time lag. Therefore, a time dependent hydrodynamic flow field can be created by spacially varying the geometry of the channel and/or by modulation of the SAW amplitude (data not show).

The basic PDMS channel was designed in a rectangular closed loop. To demonstrate the device and its usefulness for biologically relevant geometries, part of the channel has been replaced by specially designed sections of varying shape. For example, channels with bifurcations and constrictions have been prepared to mimic the branched vascular system and stenosis.

For observation, the assembled PDMS-SAW device was mounted on the stage of an inverted microscope and imaged by a fast camera (Photron, Fastcam 1024 PCI). The fluid flow field was visualized by adding small latex beads of ~1 micrometer diameter as tracer particles to the microchannel. These beads were fluorescently labeled and were observed and tracked either in phase contrast or by epi-fluorescence as shown in FIG. 5.

The pumping efficiency of the device was determined by measuring the pressure dependence on applied electric power of the IDT electrodes. The pressure was determined from experimental flow profiles. The pressure gradient was found to linearly depend on to the electric power for a wide range of power values. Hence, continuous control of the flow velocity could be achieved from no flow to 4.9 mm/s at 29 dBm electrical power, which is comparably high, with a corresponding maximum effective pressure of 4.8 Pa. The maximum volume flow rate at 4.8 Pa was determined to be about 0.15 ml/min in this particular chamber.

In one set of experiments, the pumping device presented in this example was able to pump biologically relevant samples such as red blood cell solution in 300 mOsm phosphate buffered saline (Dulbecco's PBS (1×), PAA Laboratories GmbH, 0.2 g/l KCl, 0.2 g/l $K_3PO_4$, 8.0 g/l NaCl, 1.15 g/l $Na_2HPO_4$). The fast response time of this device was used to simulate blood flow at a frequency of 60 beats/min by amplitude modulation of the voltage with a square wave signal of 1 Hz using a frequency generator (Rohde Schwarz, SML01) and to cause pumping in the circulatory channel system.

EXAMPLE 3

In this example, fluorescence-actuated sorting of 25 micrometer-diameter droplets into 3 different outlets is demonstrated. FIGS. 7A-7C show an overlay of consecutive images of a single droplet passing through the sorting device from the inlet (1) to the different outlets (2). In other words, the trajectories of a droplet going up, a droplet going straight and a droplet going down are shown to illustrate sorting into different channels or locations. It should be noted that typically, the droplets are sorted one by one. Device fabrication and operation was generally similar to that described in the previous examples, and used many of the same materials and operating conditions.

In these experiments, the fluorescence intensity of droplets was measured in a laser spot (3). Depending on fluorescence intensity, the droplets were deflected upwards (4) toward the upper outlet (FIG. 7A), downwards (5) toward the lower outlet (FIG. 7C), or not deflected and allowed to pass to the middle outlet (FIG. 7B).

The deflection was caused by an acoustic wave (excited by a tapered IDT) coupling through two different contact pads or coupling regions (6,7) into the microfluidic channel. The coupling regions were used to control the position of the acoustic coupling. Although one IDT was used in this example, in other embodiments, the acoustic wave can be generated by more than one IDT, e.g. on both sides of the channel.

The HF or resonance frequency was adjusted to selectively couple through each of the coupling regions. With the tapered IDTs used in this device, the sound path of the acoustic wave travelling along the chip depended on the HF frequency. This allowed coupling through one of the two contact pads and thereby to direct the SAW towards one of the coupling regions. In other words, acoustic coupling into the channel can occur when the HF frequency and the coupling regions correspond to the same position. Thus, by controlling the voltage applied to the IDT, the droplet could be made to be sorted into any of the 3 desired channels, as shown in FIG. 7.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An article, comprising:
   a microfluidic substrate having defined therein a microfluidic system containing an inlet microfluidic channel and more than two outlet channels meeting at a single junction;
   a tapered interdigitated transducer positioned on a material; and
   at least two coupling regions, each of which is positioned to refract surface acoustic waves generated by the tapered interdigitated transducer towards at least a portion of the single junction, wherein each coupling region physically connects the material and the microfluidic substrate.

2. The article of claim 1, comprising at least five outlet channels meeting at the single junction with the inlet microfluidic channel.

3. The article of claim 1, further comprising a surface acoustic wave generator comprising the interdigitated transducer.

4. The article of claim 1, wherein the interdigitated transducer has a finger spacing of between about 20 micrometers and about 30 micrometers.

5. The article of claim 4, wherein the interdigitated transducer comprises a first electrode and a second electrode that are interdigitated with each other.

6. The article of claim 1, wherein the material is a piezoelectric substrate.

7. The article of claim 6, wherein the piezoelectric substrate comprises $LiNbO_3$.

8. The article of claim 1, wherein the microfluidic substrate comprises polydimethylsiloxane.

* * * * *